(12) United States Patent
Sandner et al.

(10) Patent No.: US 11,508,483 B2
(45) Date of Patent: Nov. 22, 2022

(54) METHOD OF IDENTIFYING A SUBGROUP OF PATIENTS SUFFERING FROM DCSSC WHICH BENEFITS FROM A TREATMENT WITH SGC STIMULATORS AND SGC ACTIVATORS IN A HIGHER DEGREE THAN A CONTROL GROUP

(71) Applicant: ADVERIO PHARMA GMBH, Leverkusen (DE)

(72) Inventors: Peter Sandner, Wuppertal (DE); Melanie Hemmrich, Dusseldorf (DE); Janethe De Oliveira Pena, Kendall Park, NJ (US); Stephen Dawe, Grantham (GB)

(73) Assignee: Adverio Pharma GmbH, Leverkusen (DE)

(*) Notice: Subject to any disclaimer, the term of this patent is extended or adjusted under 35 U.S.C. 154(b) by 848 days.

(21) Appl. No.: 16/423,371

(22) Filed: May 28, 2019

(65) Prior Publication Data
US 2019/0371469 A1 Dec. 5, 2019

Related U.S. Application Data

(60) Provisional application No. 62/677,982, filed on May 30, 2018.

(30) Foreign Application Priority Data

Jun. 11, 2018 (EP) ..................................... 18177048

(51) Int. Cl.
G16H 50/30 (2018.01)
G16H 50/50 (2018.01)
(Continued)

(52) U.S. Cl.
CPC ........... *G16H 50/30* (2018.01); *G01N 33/564* (2013.01); *G16H 50/20* (2018.01); *G16H 50/50* (2018.01);
(Continued)

(58) Field of Classification Search
CPC combination set(s) only.
See application file for complete search history.

(56) References Cited

U.S. PATENT DOCUMENTS

| 7,209,835 | B1* | 4/2007 | Pearlman | ............... | G16H 10/40 706/54 |
| 2011/0124119 | A1* | 5/2011 | Lopes-Virella | ........ | G01N 33/92 436/501 |
| 2018/0284118 | A1* | 10/2018 | Darrah | .................... | A61P 37/06 |

FOREIGN PATENT DOCUMENTS

| EP | 2594270 | 7/2013 |
| WO | 03/095451 | 11/2003 |

(Continued)

OTHER PUBLICATIONS

Mueller, Karin, "Clinical and Histopathological Features of Patients with Systemic Sclerosis Undergoing Endomyocardial Biopsy", Plos One, May 12, 2015, pp. 1-22. (Year: 2015).*

(Continued)

*Primary Examiner* — Amber A Misiaszek
(74) *Attorney, Agent, or Firm* — Quarles & Brady LLP

(57) ABSTRACT

The present invention relates to a method of identifying a subgroup of patients suffering from diffuse cutaneous systemic sclerosis (dcSSc) which subgroup of patients benefits from a treatment with at least one sGC stimulator and/or sGC activator in a higher degree than patients not belonging to this subgroup.

10 Claims, 3 Drawing Sheets

Figure 1:
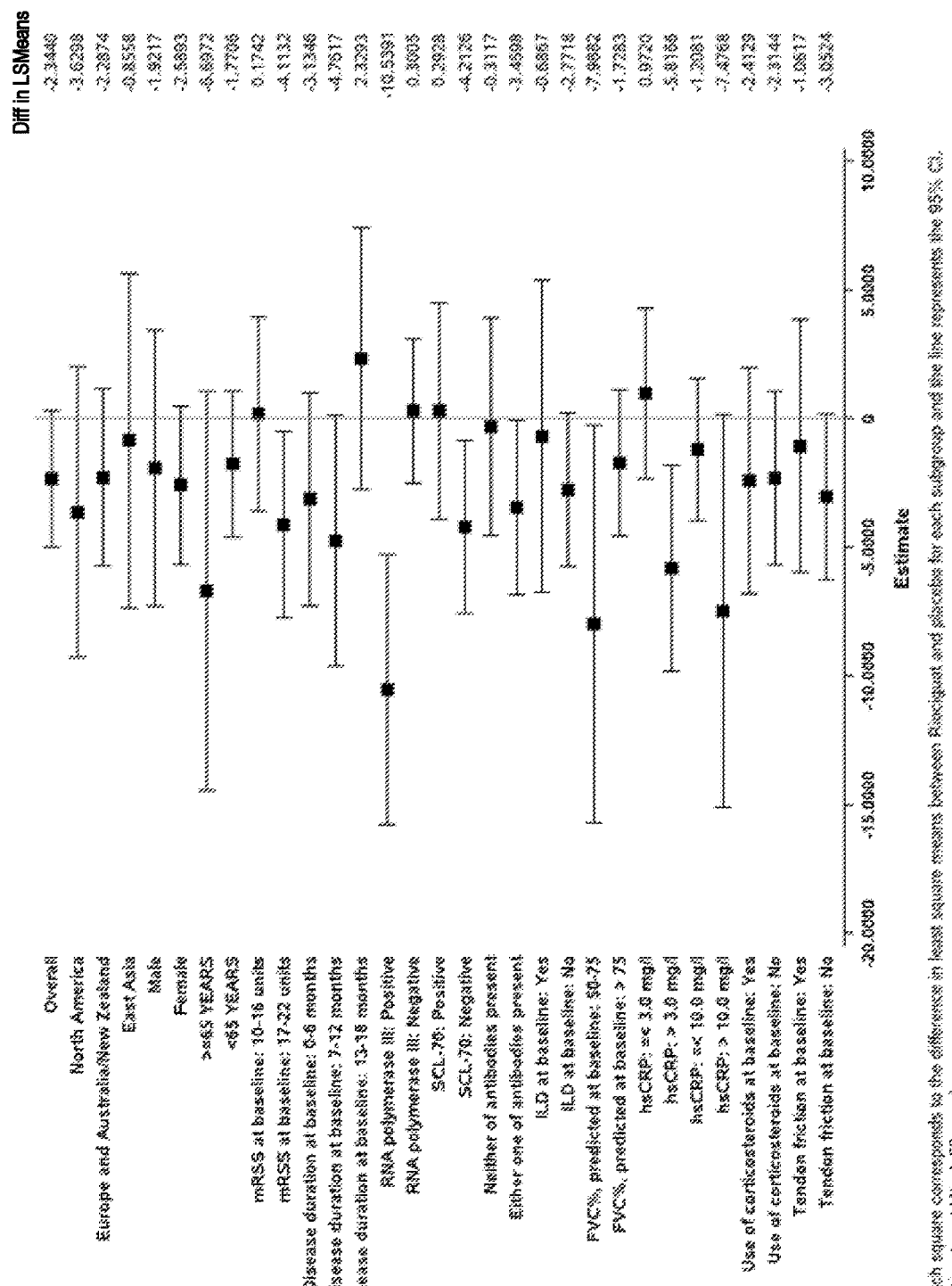

(51) Int. Cl.
G16H 50/70 (2018.01)
G16H 50/20 (2018.01)
G01N 33/564 (2006.01)

(52) U.S. Cl.
CPC ......... *G16H 50/70* (2018.01); *G01N 2800/20* (2013.01); *G01N 2800/24* (2013.01)

(56) References Cited

FOREIGN PATENT DOCUMENTS

| WO | 2011/147809 | 12/2011 |
|---|---|---|
| WO | 2011/147810 | 12/2011 |
| WO | 2012/139888 | 10/2012 |
| WO | 2014/012934 | 1/2014 |
| WO | 2014/068099 | 5/2014 |
| WO | 2016/177660 | 11/2016 |

OTHER PUBLICATIONS

European Patent Application No. 18177048.8, Extended European Search Report, dated Nov. 30, 2018, 10 pages.
Beyer et al., "Stimulation of Soluble Guanylate Cyclase Reduces Experimental Dermal Fibrosis," Annals of the Rheumatic Diseases, Jun. 2012, 71(6), pp. 1019-1026.
Beyer et al., "Stimulation of the Soluble Guanylate Cyclase (sGC) Inhibits Fibrosis by Blocking Non-Canonical TGFβ Signalling," Annals of the Rheumatic Diseases, 2015, 74(7), pp. 1408-1416.
Dees et al., "Stimulators of Soluble Guanylate Cyclase (sGC) Inhibit Experimenal Skin Fibrosis of Different Aetiologies," Annals of the Rheumatic Diseases, Dec. 2015, 74(8), pp. 1621-1625.
Distler et al., "RISE-SSc: Riociguat in Diffuse Cutaneous Systemic Sclerosis," Elsevier Respiratory Medicine, 122, pp. 14-17.
Evgenov et al., "NO-Independent Stimulators and Activators of Soluble Guanylate Cyclase: Discovery and Therapeutic Potential," Nature Reviews, Drug Discovery, Sep. 2006, 5(9), pp. 755-768.
Follmann et al., "Discovery of the Soluble Guanylate Cyclase Stimulator Vericiguat (BAY 1021189) for the Treatment of Chronic Heart Failure," J. Med. Chem., May 2017, 60(12), pp. 5146-5161.
Friebe et al., "Meeting Report of the 8th International Conference on cGMP cGMP: Generators, Effectors, and Therapeutic Implications", at Bamberg Germany, Naunyn Schmiedebergs, Arch Pharmacol, Jun. 23-25, 2017, 390(12), pp. 1177-1188.
Goh et al., "Interstitial Lung Disease in Systemic Sclerosis," Am J. Respir Care Med., Mar. 2008, 177(11), pp. 1248-1254.
Herrick et al., "Patterns and Predictors of Skin Score Change in Early Diffuse Systemic Sclerosis from the European Scleroderma Observational Study," Ann. Rheum Dis., Jan. 2018, 8 pages.
Huntgeburth et al., "Abstract: 19443: Riociguat for the Treatment of Raynaud's Phenomenon: A Single-Dose, Double-Blind, Randomised, Placebo-Controlled Cross-Over Study," Circulation, Nov. 2015, 132(Suppl. 3), 5 pages.
Khanna et al., "Minimally Important Difference in Diffuse Systemic Sclerosis: Results from the D-Penicillamine Study," Ann Rheum Dis, Mar. 2006, 65(10), pp. 1325-1329.
Khanna et al., "Safety and Efficacy of Subcutaneous Tocilizumab in Systemic Sclerosis: Results from the Open-Label period of a Phase II Randomised Controlled Trial (faSScinate)," Ann Rheum Dis, Sep. 2017, 9 pages.
Khanna et al., "Standardization of the Modified Rodnan Skin Score for Use in Clinical Trials of Systemic Sclerosis,", J Scleroderma Relat Disord., May 2017, 2(1), 18 pages.
Khanna et al., "Predictors of Lung Function Decline in Scleroderma-related Interstitial Lung Disease based on High-Resolution Computed Tomography: Implications for Cohort Enrichment in Systemic Sclerosis-Associated Interstitial Lung Disease Trials," Arthritis Research and Therapy, 2015, 17, 10 pages.
Khanna et al., "Rise-SSC: A Double-Blind, Randomised Study Evaluating the Efficacy and Safety of Riociguat for the Treatment of Patients with Diffuse Cutaneous Systemic Sclerosis," Scientific Abstracts, 2017, pp. 1271-1272.
Khanna et al., "Evidence-Based Management of Rapidly Progressing Systemic Sclerosis," Best Practice and Research Clinical Rheumatology, 2010, 24, pp. 387-400.
Lopez et al., "Anti RNAPOL and TOPOI Autoantibody Reactivity and Disease Manifestations from the Fasscinante Systemic Sclerosis Trial," Recent Advances in Therapy, 2018, 3(1S), 1 page.
Matei et al., "Protein Kinases G are Essential Downstream Mediators of the Antifibrotic Effects of sGC Stimulators," Ann Rheum Dis, Jan. 2018, pp. 459-463.
Maurer et al., "Prediction of Worsening of Skin Fibrosis in Patients with Diffuse Cutaneous Systemic Sclerosis Using the EUSTAR Database," Ann Rheum Dis, May 2015, pp. 1124-1131.
Ong et at al., "Innovative Therapies for Systemic Sclerosis," Current Opinion in Rheumatology, 2010, 22, pp. 264-272.
Pigatto et al., "Anti-RNA Polymerase III Subset of Scleroderma Patients: A Monocentric Study," Scientific Abstracts, 2017, 1 page.
Puxeddu et al., "Prognostic Scoring Systems for Clinical Course and Survival in Idiopathic Pulmonary Fibrosis," World of Journal of Respirology, Mar. 2016, 6(1), pp. 14-24.
Sandner et al., "Stimulators of Soluble Guanylate Cyclase (sGC) Improve Wound Healing in the Tsk-1 Mouse Skin Fibrosis Mode," ACR/ARHP Annual Meeting, Sep. 2015, 2 pages.
Schmidt et al., "NO- and Haem-Independent Soluble Guanylate Cyclase Activators," Handbook of Experimental Pharmacology, 2009, 191, pp. 310-339.
Shah et al., "My Approach to the Treatment of Scleroderma," Mayo Clinic Proceedings, Apr. 2013, 88(4) pp. 377-393.
Spiera et al., "Imatinib Mesylate (Gleevec) in the Treatment of Diffuse Cutaneous Systemic Scerosis: Results of a 1-Year, Phase IIa, Single-Arm, Open-Label Clinical Trial," Ann Rheum Dis, Mar. 2011, 70, pp. 1003-1009.
Stasch et al., "NO-Independent, Haem-Dependent Soluble Guanylate Cyclase Stimulators," Handbook of Experimental Pharmacology, 2009, pp. 277-308.
Steen et al., "Severe Organ Involvement in Systemic Sclerosis with Diffuse Scleroderma," Arthritis and Rheumatism, Nov. 2000, 43(11), pp. 2437-2444.
Terras et al., "RNA Polymerase III Autoantibodies may Indicate Renal and More Severe Skin Involvement in Systemic Sclerosis," International Journal of Dermatology, 2016, 55, pp. 882-885.
Wu et al., "Progression of Skin Fibrosis is Associated with Decline in Lung Function in Patients with Diffuse Cutaneous Systemic Sclerosis: A European Scleroderma Trials and Research (EUSTAR) Analysis," ACR/ARHP Annual Meeting, Sep. 2017, 4 pages.
Zenzmaier et al., "Activators and Stimulators of Soluble Guanylate Cyclase Counteract Myofibroblast Differentiation of Prostatic and Dermal Stromal Cells," Experimental Cell Research, Aug. 2015, 338(2), pp. 162-169.

\* cited by examiner

METHOD OF IDENTIFYING A SUBGROUP OF PATIENTS SUFFERING FROM DCSSC WHICH BENEFITS FROM A TREATMENT WITH SGC STIMULATORS AND SGC ACTIVATORS IN A HIGHER DEGREE THAN A CONTROL GROUP

CROSS REFERENCE TO RELATED APPLICATIONS

This application claims the benefit of U.S. Provisional Patent Application No. 62/677,982 filed on May 30, 2018, and EP Application No. 18177048.8 filed Jun. 11, 2018, both of which are hereby incorporated by reference herein in their entireties.

The present invention relates to a method of identifying a subgroup of patients suffering from diffuse cutaneous systemic sclerosis (dcSSc) which subgroup of patients benefits from a treatment with at least one sGC stimulator and/or sGC activator in a higher degree than patients not belonging to this subgroup.

The present invention further relates to at least one sGC stimulator and/or sGC activator for use in a method of preventing or delaying disease progression or for use in a method of stabilizing disease in patients suffering from diffuse cutaneous systemic sclerosis (dcSSc) and being positive for at least one marker indicating an active disease.

BACKGROUND OF THE INVENTION

Systemic sclerosis (SSc) is a generalized disorder of small arteries, microvessels and connective tissue, characterized by fibrosis and vascular obliteration in the skin and organs, particularly the lungs, heart, and digestive tract. There are two main subsets of SSc: diffuse cutaneous SSc (dcSSc) and limited cutaneous SSc (lcSSc), based on the extent of skin involvement. A third subset of SSc has also been observed, called limited systemic sclerosis (lSSc) or systemic sclerosis sine scleroderma. Limited cutaneous SSc (lcSSc) is defined as skin thickening distal to the elbows and knees, with or without involvement of the face. Diffuse cutaneous systemic sclerosis (dcSSc) is a subtype of systemic sclerosis (SSc) characterized by truncal and acral skin fibrosis with an early and significant incidence of diffuse organ involvement (interstitial lung disease, oliguric renal failure, diffuse gastrointestinal disease, and myocardial involvement).

Clinically significant major organ dysfunction often occurs early in the course of dcSSc disease. Early detection of scleroderma provides the opportunity to manage the disease process before damage and fibrosis leads to organ failure and poor outcomes. Therefore, the treatment paradigm in SSc is to treat the patients as early as possible in the active phase of the disease to prevent disease progression before irreversible damage occurs, especially in those known to be at high risk for rapid progression early on in the disease. A therapy that targets fibrosis and organ involvement before irreversible damage occurs, has the ability to improve both quality of life and survival (Shah and Wigley 2013). Skin involvement is a marker of disease activity in SSc. During the active, progressive skin phase there is an increased risk of the onset of internal organ involvement. This suggests that active systemic disease and organ injury may be clinically silent but biologically underway during the early clinically obvious progressive skin disease. In diffuse scleroderma, most new organ involvement (gastrointestinal, lung, heart and kidney) occurs within the first 3 years of disease onset (Steen and Medsger 2000).

SSc has a broad variety of symptoms triggered by excessive deposition of extracellular matrix in the dermis resulting in skin fibrosis. In later stages, SSc is characterized by progressive tissue fibrosis affecting other internal organs as the lung, the kidney, or the heart. Therefore systemic sclerosis is the hallmark of the disease comprising also e.g. lung fibrosis, renal fibrosis, fibrosis of the heart, or the blood vessels. Besides excessive fibrosis in the skin and internal organs, SSc is also characterized by vasculopathies and microangiopathies. Especially small vessel vasculopathies and concomitant vascular malperfusion and ischemia can cause Raynaud's phenomena (RP) but may also to the formation of digital ulcer (DU).

Whereas tissue fibrosis can cause end organ failure and lead to high morbidity and mortality in patients with end-stage SSc, formation of DU substantially reduce the quality of life of SSc patients, impairs hand function and leads to disability.

In dcSSc, the skin of the proximal extremities and the trunk are also affected, and skin fibrosis becomes rapidly generalized. Edematous skin, carpal tunnel syndrome, Raynaud's phenomenon (RP), and painful joints may be the earliest manifestations.

Digital ulcers (DUs) are a common visible manifestation of the progressive vascular disease that characterizes the SSc disease process. DUs not only impact significantly on patients' quality of life and hand function, but are also a biomarker of internal organ involvement and of disease severity.

The pathogenesis of systemic sclerosis (SSc) and diffuse cutaneous SSc (dcSSc) is still unclear. However, it is known that systemic sclerosis is a non-inherited, noninfectious disease and thought to be an autoimmune disease, characterized by heterogeneous clinical features and variable disease course. Specific antinuclear antibodies (ANA) identify different clinical subsets and are very useful in defining the prognosis of the patients. Recently, anti-RNA polymerase III autoantibodies were defined as the third specific ANA of SSc, together with anti-centromere (ACA) and anti-topoisomerase I (anti-Scl70). In predictive models for mRSS progression in patients suffering from dcSSc, Herrick et al. (2018) reported that anti-RNA polymerase III autoantibodies are a marker for an active disease, especially early in the course of the disease, and patients with these autoantibodies are more likely to rapidly progress than other subgroups. The presence of anti-RNA polymerase III autoantibodies was shown to identify a subset of SSc patients characterized by a severe clinical picture, with a high prevalence of the diffuse cutaneous form, scleroderma renal crisis (SRC), cardiac involvement and interstitial lung disease (ILD) (Pigatto et al. 2017). Another study concluded that the detection of anti-RNA polymerase III autoantibodies in patients with SSc correlates with renal crisis and severe cutaneous involvement (Terras et al., 2016).

A further known marker for an active dcSSc disease is an elevated hsCRP. A hsCRP of >3 mg/L is considered as elevated. The term "CRP" refers to the C-reactive protein. The hsCRP test is a highly sensitive test for quantification of CRP, an acute-phase protein released into the blood by the liver during e.g. inflammation, infection, trauma, necrosis, malignancy, and allergic reaction. An elevated hsCRP has also been associated with the presence of heart disease. A hsCRP of >3.0 mg/L is considered as indicating a high risk of developing cardiovascular disease.

A further known marker for an active dcSSc disease is a decreased forced vital capacity (FVC) % predicted at baseline of 50-75 that indicates potential lung fibrosis and/or ILD in SSc patients. FVC % predicted is calculated as percentage of expected, normal FVC, based e.g. on the age, gender and sometimes other information of the patient according to the formula: FVC % predicted=Measured value FVC/Predicted value FVC×100. The presence of moderate-to-severe fibrosis at baseline was suggested to predict poor survival in patients with SSc-ILD (Goh et al., 2008).

Within the meaning of the present invention, the terms decrease and decline of FVC % predicted are used synonymously.

The modified Rodnan skin score (mRSS), which is a measure of skin thickness, is used as a primary or secondary outcome measure in clinical trials of dcSSc. Further measures indicating treatment efficacy include the reduction of organ involvement such as interstitial lung disease (ILD), measured by the decline of the lung function (FVC % predicted), cardiac involvement including pulmonary hypertension, gastrointestinal disease (GI) and scleroderma renal crisis (SRC). Interstitial lung disease (ILD) is a broad category of lung diseases that includes more than 130 disorders. Common characteristics of ILD are scarring (pulmonary fibrosis) and/or inflammation of the lungs. Forced vital capacity (FVC) is used as a measure to evaluate the lung function in ILD. mRSS progression and a decrease of FVC of equal to or more than −10% has been shown to be associated with lower probability for survival (Wu et al, 2017).

No disease-modifying therapies have been approved for the treatment of patients with SSc to date, but some may control symptoms. Treatment options for patients with SSc are largely dependent on the organs affected. Methotrexate, mycophenolate mofetil, cyclophosphamide, or azathioprine are widely used. A survey conducted by the Scleroderma Clinical Trials Consortium (SCTC) and Canadian Scleroderma Research Group (CSRG) to gain a consensus from SSc experts worldwide also recommended these agents in the management of SSc. In recent years methotrexate and mycophenolate mofetil have been used as first and second line treatments, respectively, for skin involvement in SSc, with the former becoming the first line treatment for ILD. The criteria for when to use rescue therapy also widely reflect the recommendations on Systemic Sclerosis Disease Modification Clinical Trials Design.

More recently kinase inhibitors and anti-inflammatory drugs are under investigation as immunosuppressant and antifibrotic agents in SSc, but tolerability is limited in SSc patients (Khanna and Denton 2010, Ong and Denton 2010, Spiera 2011). In a clinical Phase 2 study (fasSScinate), the safety and efficacy of subcutaneous tocilizumab, an immunomodulating drug, in systemic sclerosis was assessed. Tocilizumab is a monoclonal anti-IL-6 receptor-α antibody approved e.g. for the treatment of patients with rheumatoid arthritis. In the study report it was concluded that skin score improvement and FVC stabilization in the double-blind period were observed in placebo-treated patients who transitioned to tocilizumab (Khanna et al., 2017a).

These therapies either used as stand-alone treatment or combined are of limited efficacy and exhibit considerable side effects. Therefore alternative treatment options in SSc, in particular dcSSc which are efficacious and safer are urgently needed.

It is well accepted that sGC stimulators act via direct stimulation of the sGC which does not require NO. The sGC stimulators bind to the alpha subunit of the non-oxidized and haem-containing sGC which leads to NO-independent formation and increase of intracellular cGMP (Stasch & Hobbs 2009). In addition, the sGC stimulators enhance the NO-effect on cGMP when NO is bound to the sGC. Therefore, sGC stimulators also exhibit synergistic effects with NO on cGMP production. The indazole derivative YC-1 was the first NO-independent but haem-dependent sGC stimulator described (Evgenov et al., 2006). Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and Riociguat (BAY 63-2521). Together with the structurally different substances CFM-1571 and A-350619, these compounds form the class of the sGC stimulators (Evgenov et al., 2006; Stasch and Hobbs, 2009). More recently further compound classes were discovered which show a different pharmacokinetic profile and also a different organ distribution which might have an impact on their treatment potential (Follmann et al. J. Med Chem 2017).

Under oxidative stress conditions, the $Fe^{2+}$ iron atom of the haem group of the sGC is oxidized to $Fe^{3+}$ which destabilizes the binding of the haem group to the beta-subunit of the sGC and renders the enzyme haem-free. With the discovery of BAY 58-2667 (Cinaciguat) a new chemical matter has been found which is able to activate haem-free sGC. Therefore, BAY 58-2667 is the prototype of this class of sGC activators. Common characteristics of these substances are that in combination with NO they only have an additive effect on enzyme activation, and that the activation of the oxidized or haem-free enzyme is markedly higher than that of the haem-containing enzyme (Schmidt et al. 2009). Spectroscopic studies show that BAY 58-2667 displaces the oxidized haem group which, as a result of the weakening of the iron-histidine bond, is attached only weakly to the sGC. It has also been shown that the characteristic sGC haem binding motif Tyr-x-Ser-x-Arg is absolutely essential both for the interaction of the negatively charged propionic acids of the haem group and for the action of BAY 58-2667. Therefore, it is assumed that the binding site of BAY 58-2667 at the sGC is identical to the binding site of the haem group (Schmidt et al. 2009).

It is well established that sGC stimulators and sGC activators lead to relaxation of vascular smooth muscle cells and blood pressure decrease. This is one of the basic principles for the use of sGC stimulators in cardiovascular diseases. However, other modes of action beyond vasodilation and targeting the vascular smooth muscle cells are only partly understood and are currently under investigation (Friebe et al. 2017). In addition, it is also not well described in the art in which diseases and under which conditions and in which tissue or cell the increased oxidative stress leads to formation of haem-free sGC. It is difficult to predict the cellular effects and treatment effects of sGC stimulators and sGC activators since cGMP has multiple downstream targets, e.g. protein kinases, phosphodiesterases, ion channels, structural proteins, and potentially also unknown targets, which vary from cell to cell and from tissue to tissue and could also be substantially down- or upregulated in disease states.

More recently, antifibrotic effects of sGC stimulators and sGC activators have been shown and sGC stimulators have been tested in various preclinical mouse models of skin fibrosis. In particular, it could be demonstrated in vitro that sGC stimulators, like BAY 41-2272 and Riociguat, could reduce collagen production in human dermal fibroblasts of SSc patients (Beyer et al. 2012). Moreover, sGC stimulators reduced fibroblast-to-myofibroblast differentiation in human dermal fibroblasts, and reduced established myofibroblasts (Zenzmaier et al. 2015). These aforementioned in vitro data were translated into in vivo preclinical models of skin fibrosis. It has been demonstrated that sGC stimulators, like BAY 41-2272, prevented the progression of TGFβ-induced skin fibrosis which mechanistically confirmed previous in vitro findings (Beyer et al. 2015). Moreover, it was demonstrated that sGC stimulators prevented the progression of skin fibrosis in a bleomycin model and in the genetic TSK-1 mouse model (Beyer et al. 2012, Dees et al. 2015). In addition, sGC stimulators reduced skin and intestinal fibrosis in the chronic graft-versus-host disease (cGvHD) model which is characterized by skin fibrosis but also fibrosis of the gut. More recently it was also shown that sGC stimulation fails to prevent bleomycin-induced skin fibrosis in PKG1 and PKG2 knockout mice, strongly suggesting that the effects are mediated via protein kinases G (PKG) (Matei et al. 2018). In summary, these data demonstrated a dose-dependent prevention of the development of skin fibrosis in a broad range of potential disease etiologies ranging from TGFβ overexpression and inflammation caused by bleomycin to non-inflammatory background as present in the TSK-1 mice but also to skin fibrosis and fibrosis of internal organs caused by allogenic bone-marrow transplantation (cGvHD). These data suggest a prevention of the progression of skin fibrosis in mice. Therefore, sGC stimulators might have beneficial effects in SSc patients with skin fibrosis. WO 2011/147810 and EP 2594270 pertain to the use of sGC stimulators or sGC activators alone and combinations with PDE5 inhibitors for the treatment of systemic sclerosis (SSc), and WO 2016/177660 pertains to the use of sGC stimulators or sGC activators, alone and in combination with PDE5 inhibitors for the treatment of Digital Ulcers (DU) concomitant to systemic sclerosis (SSc). These patent applications only provide animal data. However, clinical data on the treatment of dcSSC are elusive and it is not established that mouse models reflect the human situation. In particular, it is still unknown whether subgroups of the dcSSc patient population may respond to treatment with at least one sGC stimulator and/or sGC activator in a surprising manner, being unexpectedly responsive or unresponsive.

Therefore, it is one object of the invention to provide a method that allows to identify a subgroup of patients suffering from diffuse cutaneous systemic sclerosis (dcSSc) which subgroup of patients benefits from a treatment with at least one sGC stimulator and/or sGC activator in a higher degree than patients not belonging to this subgroup.

INVENTION

One embodiment of the present invention is a method for identifying a subgroup of patients suffering from diffuse cutaneous systemic sclerosis (dcSSc) which subgroup of patients benefits from a treatment with at least one sGC stimulator and/or sGC activator or a pharmaceutically acceptable salt thereof in a higher degree than patients not belonging to this subgroup, comprising the steps of
a. measuring at least one marker selected from the group consisting of the presence or absence of anti-RNA polymerase III autoantibodies, a hsCRP at baseline, and a FVC % predicted at baseline and
b. allocating those patients to the above mentioned subgroup that show one or more of the presence of anti-RNA polymerase III autoantibodies, a hsCRP at baseline of >3 mg/L, and a FVC % predicted at baseline of 50-75.

Within the meaning of the invention, the at least one marker selected from the group consisting of the presence of anti-RNA polymerase III autoantibodies, of hsCRP at baseline of >3 mg/L, and FVC % predicted at baseline of 50-75 is a marker indicating active disease.

"Baseline" within the meaning of the present invention means at the start of the study and before randomization and before the first treatment with at least one sGC stimulator and/or sGC activator.

The term "active disease" is defined as a phase of the disease, where early and rapid progression of the disease in skin and internal organs occurs. Subgroups indicative of more active and progressive disease include patients being positive for anti-RNA polymerase antibodies and/or having activity markers such as high inflammatory profile indicated by an elevation of hsCRP, presence of joint involvement and tendon friction rubs, lower mRSS in combination with a short disease duration of ≤18 months and progression of skin fibrosis (Herrick et al, 2018; Maurer et al., 2015).

The term "lung function" refers to the function of the lungs is the process of gas exchange called respiration (or breathing). In respiration, oxygen from incoming air enters the blood, and carbon dioxide, a waste gas from the metabolism, leaves the blood. A reduced lung function means that the ability of lungs to exchange gases is reduced. The lung function test is designed to measure how well the lungs are working. Abbreviated PFT. PFTs gauge how the lungs are expanding and contracting (when a person inhales and exhales) and measure the efficiency of the exchange of oxygen and carbon dioxide between the blood and the air within the lungs. The FVC % predicted and DLco are part of the lung function tests.

The term "FVC % predicted" refers to the forced vital capacity and is the maximal volume of gas that can be exhaled from full inhalation by exhaling as forcefully and rapidly as possible. The FVC % predicted is reduced in lung disease, including ILD in SSc and is a predictor for survival.

The term "ILD" refers to interstitial lung disease that includes a group of diseases that have thickening of the supporting tissues between the air sacs of the lungs. Pulmonary manifestations of SSc include interstitial lung disease (fibrosis).

The term "treating" or "treatment" as used in the present invention refers to alleviating or abrogating the cause and/or effects or symptoms or clinical manifestations of the disorder or disease. More specifically, as used herein, the terms "treating" or "treatment" refer to the reduction or amelioration or slowing down of the progression, severity and/or duration of diffuse cutaneous systemic sclerosis. In some embodiments, the terms "treating" or "treatment" refer to the reduction, amelioration or slowing down of the progression, the severity and/or the duration of one or more physical symptoms or clinical manifestations (preferably, one or more measurable physical symptoms or clinical manifestations) of the condition, as a result of the administration of one or more therapies (e.g., at least one sGC activator or sGC stimulator selected from one of the groups specified above or a pharmaceutically acceptable salt thereof, either alone or in combination therapy). In some embodiments, "treating" or "treatment" may result in total or partial reversal of the disease (i.e., as determined by normalization of the clinical parameters, findings or manifestations associated with the disease). In other embodiments, "treating" or "treatment" may result in slowing down or halting the progression of diffuse cutaneous systemic sclerosis. For example, this can include preventing or delaying disease progression and/or stabilizing of disease in patients suffering from diffuse cutaneous systemic sclerosis (dcSSc) and being positive for at least one marker indicating an active disease. In particular, the preventing or delaying disease progression and/or stabilizing of disease is characterized by preventing or delaying progression and/or stabilizing of skin fibrosis, of dcSSc concomitant fibrosis of internal organs, comprising the lung, the kidney, the heart, and the blood vessels, and of improving, i.e. decreasing, the score of an HAQ-DI.

In some embodiments, the terms "treating" or "treatment" refer to delaying the onset of dcSSc in a patient in need thereof. In some embodiments, the terms "treating" or "treatment" refer to delaying the onset of a physical symptom or set of physical symptoms or clinical manifestations or findings associated with dcSSc.

One embodiment of the present invention is a method for identifying a subgroup of patients suffering from diffuse cutaneous systemic sclerosis (dcSSc) which subgroup of patients benefits from a treatment with at least one sGC stimulator selected from the group consisting of
methyl 4,6-diamino-2-[1-(2-fluorobenzyl)-1H-pyrazolo[3,4-b]pyridin-3-yl]-5-pyrimidinyl(methyl)carbamate (Riociguat)
methyl 4,6-diamino-2-[1-(2-fluorobenzyl)-1H-pyrazolo[3,4-b]pyridin-3-yl]-5-pyrimidinylcarbamate (Nelociguat)
methyl {4,6-diamino-2-[5-fluoro-1-(2-fluorobenzyl)-1H-pyrazolo[3,4-b]pyridine-3-yl]pyrimidin-5-yl}carbamate (Vericiguat)
ent-N-[(2S)-amino-2-methylbutyl]-8-[(2,6-difluorobenzyl)oxy]-2,6-dimethylimidazo[1,2-a]pyridine-3-carboxamide (enantiomer A).
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat),
or a pharmaceutically acceptable salt thereof, in a higher degree than patients not belonging to this subgroup, comprising the steps of
a. measuring at least one marker selected from the group consisting of the presence or absence of anti-RNA polymerase III autoantibodies, a hsCRP at baseline, and a FVC % predicted at baseline and
b. allocating those patients to the above mentioned subgroup that show one or more of the presence of anti-RNA polymerase III autoantibodies, a hsCRP at baseline of >3 mg/L, and FVC % predicted at baseline of 50-75.

One embodiment of the present invention is a method for identifying a subgroup of patients suffering from diffuse cutaneous systemic sclerosis (dcSSc) which subgroup of patients benefits from a treatment with at least one sGC activator selected from the group consisting of
3-(4-chloro-3-{[(2S,3R)-2-(4-chlorophenyl)-4,4,4-trifluoro-3-methylbutanoyl]amino}phenyl)-3-cyclopropylpropanoic acid,
4-({(4-carboxybutyl) [2-(5-fluoro-2-{[4'-(trifluoromethyl) [1,1'-biphenyl]-4-yl]methoxy}phenyl)ethyl]amino}methyl)benzoic acid,
5-{(4-carboxybutyl) [2-(2-{[3-chloro-4'-(trifluoromethyl)biphenyl-4-yl]methoxy}phenyl)ethyl]amino}-5,6,7,8-tetrahydroquinoline-2-carboxylic acid, and
5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid
or a pharmaceutically acceptable salt thereof, in a higher degree than patients not belonging to this subgroup, comprising the steps of
a. measuring at least one marker selected from the group consisting of the presence or absence of anti-RNA polymerase III autoantibodies, a hsCRP at baseline, and a FVC % predicted at baseline and
b. allocating those patients to the above mentioned subgroup that show one or more of the presence of anti-RNA polymerase III autoantibodies, a hsCRP at baseline of >3 mg/L, and a FVC % predicted at baseline of 50-75.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazzol[3,4-b]pyridin-3-yl]-5-pyrimidinyl(methyl) carbamate (Riociguat) or a pharmaceutically acceptable salt thereof in a higher degree than patients not belonging to this subgroup, comprising the steps of
a. measuring at least one marker selected from the group consisting of the presence or absence of anti-RNA polymerase III autoantibodies, hsCRP at baseline, and FVC % predicted at baseline and
b. allocating those patients to the above mentioned subgroup that show one or more of the presence of anti-RNA polymerase III autoantibodies, hsCRP at baseline of >3 mg/L, and FVC % predicted at baseline of 50-75.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of
a. measuring the presence or absence of anti-RNA polymerase III autoantibodies and
b. allocating those patients to the above mentioned subgroup that show the presence of anti-RNA polymerase III autoantibodies.

One embodiment of the present invention is a method for identifying a subgroup of patients suffering from diffuse cutaneous systemic sclerosis (dcSSc) which subgroup of patients benefits from a treatment with at least one sGC stimulator and/or sGC activator in a higher degree than patients not belonging to this subgroup, comprising the steps of
a. measuring FVC % predicted at baseline and
b. allocating those patients to the above mentioned subgroup that show FVC % predicted at baseline of 50-75.

One embodiment of the present invention is a method for identifying a subgroup of patients suffering from diffuse cutaneous systemic sclerosis (dcSSc) which subgroup of patients benefits from a treatment with at least one sGC stimulator and/or sGC activator in a higher degree than patients not belonging to this subgroup, comprising the steps of
a. measuring hsCRP at baseline and
b. allocating those patients to the above mentioned subgroup that show hsCRP at baseline of >3 mg/L.

One embodiment of the present invention is a method for identifying a subgroup of patients suffering from diffuse cutaneous systemic sclerosis (dcSSc) which subgroup of patients benefits from a treatment with at least one sGC stimulator and/or sGC activator in a higher degree than patients not belonging to this subgroup, comprising the steps of
a. measuring hsCRP at baseline and
b. allocating those patients to the above mentioned subgroup that show hsCRP at baseline of >10 mg/L.

One embodiment of the present invention is a method for identifying a subgroup of patients suffering from diffuse cutaneous systemic sclerosis (dcSSc) which subgroup of patients benefits from a treatment with methyl 4,6-diamino- 2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of the presence or absence of anti-RNA polymerase III autoantibodies and FVC % predicted at baseline and b. allocating those patients to the above mentioned subgroup that show the presence of anti-RNA polymerase III autoantibodies and FVC % predicted at baseline of 50-75.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of the presence or absence of anti-RNA polymerase III autoantibodies and hsCRP at baseline and b. allocating those patients to the above mentioned subgroup that show the presence of anti-RNA polymerase III autoantibodies and hsCRP at baseline of >3 mg/L.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of the presence or absence of anti-RNA polymerase III autoantibodies and hsCRP at baseline and b. allocating those patients to the above mentioned subgroup that show the presence of anti-RNA polymerase III autoantibodies and hsCRP at baseline of >10 mg/L.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of hsCRP at baseline, and FVC % predicted at baseline and b. allocating those patients to the above mentioned subgroup that show hsCRP at baseline of >3 mg/L and FVC % predicted at baseline of 50-75.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of hsCRP at baseline, and FVC % predicted at baseline and b. allocating those patients to the above mentioned subgroup that show hsCRP at baseline of >10 mg/L and FVC % predicted at baseline of 50-75.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of the presence or absence of anti-RNA polymerase III autoantibodies, hsCRP at baseline, and FVC % predicted at baseline and b. allocating those patients to the above mentioned subgroup that show the presence of anti-RNA polymerase III autoantibodies, hsCRP at baseline of >3 mg/L, and FVC % predicted at baseline of 50-75.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring the group of markers consisting of the presence or absence of anti-RNA polymerase III autoantibodies, hsCRP at baseline, and FVC % predicted at baseline and b. allocating those patients to the above mentioned subgroup that show the presence of anti-RNA polymerase III autoantibodies, hsCRP at baseline of >10 mg/L, and FVC % predicted at baseline of 50-75.

The parameters for measuring the preventing or delaying of disease progression and/or stabilizing of disease in patients suffering from diffuse cutaneous systemic sclerosis (dcSSc) include the development in mRSS units, changes in FVC % predicted and/or in patient-related outcomes (PROs), such as the score of the Health Assessment Questionnaire disability index (HAQ-DI).

The Health Assessment Questionnaire-disability index (HAQ-DI) is a well-accepted measure of disability and physical function which has been included in numerous labels for products approved for various rheumatic diseases and is also used as measure of disability and physical function in dcSSc. The HAQ-DI assesses a patient's level of functional ability and includes questions on fine movements of the upper extremity, locomotor activities of the lower extremity, and activities that involve both upper and lower extremities. There are 20 questions in eight categories of functioning which represent a comprehensive set of functional activities—dressing, rising, eating, walking, hygiene, reach, grip, and usual activities. Two additional questions ask patients whether they require any aids or devices, or help from a person to be able to help them undertake these activities. The HAQ-DI has a range from 0-3 (from 0 to 1: mild difficulties to moderate disability; from 1 to 2: disability moderate to severe; from 2 to 3: severe to very severe disability). The HAQ-DI has been found to have clinically meaningful thresholds as follows: −0.21 for improvement and +0.21 for worsening (Khanna et al. 2006).

One embodiment of the present invention is a method for identifying a subgroup of patients suffering from diffuse cutaneous systemic sclerosis (dcSSc) which subgroup of patients benefits from a treatment with at least one sGC stimulator selected from the group consisting of methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A).

1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof, in a higher degree than patients not belonging to this subgroup, comprising the steps of a. measuring at least one marker selected from the group consisting of the presence or absence of anti-RNA polymerase III autoantibodies, hsCRP at baseline, and FVC % predicted at baseline and b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with at least one of the above mentioned sGC stimulators is defined as a higher degree of at least one of delaying or preventing progression or stabilizing of one or more of skin fibrosis, of dcSSc concomitant fibrosis of internal organs, comprising the lung, the kidney, the heart, and the blood vessels, and of decreasing the score of the HAQ-DI as compared to patients not belonging to this subgroup.

One embodiment of the present invention is a method for identifying a subgroup of patients suffering from diffuse cutaneous systemic sclerosis (dcSSc) which subgroup of patients benefits from a treatment with at least one sGC activator selected from the group consisting of 3-(4-chloro-3-{[(2S,3R)-2-(4-chlorophenyl)-4,4,4-trifluoro-3-methylbutanoyl]amino}phenyl)-3-cyclopropylpropanoic acid, 4-({(4-carboxybutyl) [2-(5-fluoro-2-{[4'-(trifluoromethyl)[1,1'-biphenyl]-4-yl]methoxy}phenyl)ethyl]amino}methyl)benzoic acid, 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid, and 5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid or a pharmaceutically acceptable salt thereof, in a higher degree than patients not belonging to this subgroup, comprising the steps of a. measuring at least one marker selected from the group consisting of the presence or absence of anti-RNA polymerase III autoantibodies, hsCRP at baseline, and FVC % predicted at baseline and b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with at least one sGC activator mentioned above or a pharmaceutically acceptable salt thereof is defined as a higher degree of at least one of delaying or preventing progression or stabilizing of one or more of skin fibrosis, of dcSSc concomitant fibrosis of internal organs, comprising the lung, the kidney, the heart, and the blood vessels, and of decreasing the score of the HAQ-DI as compared to patients not belonging to this subgroup.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring at least one marker selected from the group consisting of the presence or absence of anti-RNA polymerase III autoantibodies, hsCRP at baseline, and FVC % predicted at baseline and b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with methyl 4,6-diamino-2-[1-(2-fluorobenzyl)-1H-pyrazolo[3,4-b]pyridin-3-yl]-5-pyrimidinyl(methyl)carbamate (Riociguat) is defined as a higher degree of at least one of delaying or preventing progression or stabilizing of one or more of skin fibrosis, of dcSSc concomitant fibrosis of internal organs, comprising the lung, the kidney, the heart, and the blood vessels, and of decreasing the score of the HAQ-DI as compared to patients not belonging to this subgroup.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring at least one marker selected from the group consisting of the presence or absence of anti-RNA polymerase III autoantibodies, hsCRP at baseline, and FVC % predicted at baseline and b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with methyl 4,6-diamino-2-[1-(2-fluorobenzyl)-1H-pyrazolo[3,4-b]pyridin-3-yl]-5-pyrimidinyl(methyl)carbamate (Riociguat) as compared to patients not belonging to this subgroup is defined as a higher degree of delaying or preventing of progression or stabilizing of skin fibrosis, measured as mRSS score.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of a. measuring at least one marker selected from the group consisting of the presence or absence of anti-RNA polymerase III autoantibodies, hsCRP at baseline, and FVC % predicted at baseline and
b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with methyl 4,6-diamino-2-[1-(2-fluorobenzyl)-1H-pyrazolo[3,4-b]pyridin-3-yl]-5-pyrimidinyl(methyl)carbamate (Riociguat) as compared to patients not belonging to this subgroup is defined as a higher degree of delaying or preventing of progression or stabilizing of dcSSc concomitant fibrosis of the lung, measured as FVC % predicted.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of
a. measuring at least one marker selected from the group consisting of the presence or absence of anti-RNA polymerase III autoantibodies, hsCRP at baseline, and FVC % predicted at baseline and
b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with methyl 4,6-diamino-2-[1-(2-fluorobenzyl)-1H-pyrazolo[3,4-b]pyridin-3-yl]-5-pyrimidinyl(methyl)carbamate (Riociguat) as compared to patients not belonging to this subgroup is defined as a higher degree of preventing or delaying progression or stabilizing of dcSSc, measured by HAQ-DI.

One embodiment of the present invention is a method for identifying a subgroup of patients suffering from diffuse cutaneous systemic sclerosis (dcSSc) which subgroup of patients benefits from a treatment with methyl 4,6-diamino-2-[1-(2-fluorobenzyl)-1H-pyrazolo[3,4-b]pyridin-3-yl]-5-pyrimidinyl(methyl) carbamate (Riociguat) or a pharmaceutically acceptable salt thereof in a higher degree than patients not belonging to this subgroup, comprising the steps of
a. measuring at least one marker selected from the group consisting of the presence or absence of anti-RNA polymerase III autoantibodies, hsCRP at baseline, and FVC % predicted at baseline and
b. allocating those patients to the above mentioned subgroup that show one or more of the presence of anti-RNA polymerase III autoantibodies, hsCRP at baseline of >3 mg/L, and FVC % predicted at baseline of 50-75, wherein a higher degree of benefit of the above defined subgroup of patients from a treatment with methyl 4,6-diamino-2-[1-(2-fluorobenzyl)-1H-pyrazolo[3,4-b]pyridin-3-yl]-5-pyrimidinyl(methyl)carbamate (Riociguat) as compared to patients not belonging to this subgroup is defined as a higher degree of preventing or delaying of progression or stabilizing of dcSSc, measured as mRSS score and as FVC % predicted.

According to the present invention, preventing or delaying disease progression is defined as preventing an increase of the mRSS of ≥4 units from baseline to week 12-120, or from baseline to week 12-60, or from baseline to week 12-52, or from baseline to week 39-52, or from baseline to week 52, and stabilizing the disease is defined as a change of the mRSS of −3 to 3 from baseline to week 12-120, or from baseline to week 12-80, or from baseline to week 12-52, or from baseline to week 39-52, or from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

According to the present invention, preventing or delaying of progression or stabilizing of skin fibrosis is measured as mRSS score, wherein preventing or delaying disease progression is defined as preventing an increase of the mRSS of ≥4 units from baseline to week 12-52, and stabilizing the disease is defined as a change of the mRSS of −3 to 3 from baseline to week 12-52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

According to the present invention, preventing or delaying of progression or stabilizing of skin fibrosis is measured as mRSS score, wherein preventing or delaying disease progression is defined as preventing an increase of the mRSS of ≥4 units from baseline to week 52, and stabilizing the disease is defined as a change of the mRSS of −3 to 3 from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

A change of mRSS −3 to 3 from baseline to week 12-120, or from baseline to week 12-80, or from baseline to week 12-52, or from baseline to week 39-52, or from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat) is defined as almost no change of the mRSS.

According to the present invention, preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 12-120, or from baseline to week 12-80, or from baseline to week 12-52, or from baseline to week 39-52, or from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

According to the present invention, preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 12-52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

According to the present invention, preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, the term "preventing or delaying a decrease in FVC % predicted of equal to or more than −10 from baseline to a defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat)" has the meaning that the lung function as measured by FVC % predicted does not decrease or decline by more than 10% from baseline to the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, the term "preventing or delaying a decrease in FVC % predicted of equal to or more than −10 from baseline to a defined time or time range [weeks] of treatment with at least one sGC stimulator and/or sGC activator" has the meaning that the lung function as measured by FVC % predicted does not decrease or decline by more than 10% from baseline to the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, the terms decrease and decline of FVC % predicted are used synonymously.

In other words, if a patient has a FVC % predicted at baseline of 75, the term "preventing or delaying a decrease in FVC % predicted of equal to or more than −10 from baseline to a defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat)" has the meaning that the lung function of this patient as measured by FVC % predicted does not decrease or decline to 65 or less from baseline to the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat).

In other words, if a patient has a FVC % predicted at baseline of 75, the term "preventing a decrease in FVC % predicted of equal to or more than −10 from baseline to a defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat)" has the meaning that the lung function of this patient as measured by FVC % predicted will be more than 65 at the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured by HAQ-DI, wherein preventing or delaying disease progression and/or stabilizing disease is defined as a decrease in HAQ-DI of more than −0.21 from baseline to week 12-120, or from baseline to week 12-80, or from baseline to week 12-52, or from baseline to week 39-52, or from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured by HAQ-DI, wherein preventing or delaying disease progression and/or stabilizing disease is defined as a decrease in HAQ-DI of more than −0.21 from baseline to week 12-52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured by HAQ-DI, wherein preventing or delaying disease progression and/or stabilizing disease is defined as a decrease in HAQ-DI of more than −0.21 from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, the terms decrease and decline in HAQ-DI are used synonymously.

Within the meaning of the present invention, the term "decrease in HAQ-DI of more than −0.21 from baseline to a defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat)" has the meaning that the HAQ-DI decreases or declines by more than −0.21 from baseline to the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, the term "decrease in HAQ-DI of more than −0.21 from baseline to a defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat)" has the meaning that the HAQ-DI decreases or declines by more than −0.21 from baseline to the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat).

In other words, if a patient has a HAQ-DI at baseline of 0.970, the term "decrease in HAQ-DI of more than −0.21 from baseline to a defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat)" has the meaning that the HAQ-DI of this patient decreases or declines to a value of below 0.760 from baseline to the defined time or time range [weeks] of treatment with methyl 4,6-diamino-2-[1-(2-fluorobenzyl)-1H-pyrazolo[3,4-b]pyridin-3-yl]-5-pyrimidinyl(methyl)carbamate (Riociguat) ator.

dcSSc patients that are positive for anti-RNA polymerase III autoantibodies and which are known for a particularly aggressive disease progression early in the disease, surprisingly not only benefit significantly from a treatment with Riociguat but benefit in a higher degree than patients that are not positive for anti-RNA polymerase III autoantibodies. Said benefit comprises a delay or prevention of the progression of skin fibrosis and/or a stabilization of the skin fibrosis as indicated in the mRSS. In addition, fewer dcSSc patients that are positive for anti-RNA polymerase III autoantibodies showed a decrease of lung function (measured as FVC % predicted) of equal to or more than −10% from baseline to week 52 of treatment with Riociguat (−10% under Riociguat treatment vs −15.4% under placebo, respectively). No decline of lung function (FVC % predicted) was seen in the Riociguat group (+1.2) at week 52 compared to baseline and a worsening of the FVC % predicted in the placebo group (−3.7). A higher decline of FVC is related to a lower probability of survival.

This result could not be expected, as it is for example in contrast to the results of a Phase 2 study on Tocilizumab (fasSScinate), where the anti-RNA polymerase III autoantibody profile had little clinically meaningful influence on the effect of Tocilizumab on change in mRSS or ppFVC at week 48 (Lopez et al. 2018).

The present invention also shows that dcSSc patients that have a FVC % predicted at baseline of 50-75 and which are known for a lower probability of survival, surprisingly not only benefit significantly from a treatment with Riociguat but benefit in a higher degree than patients that show a FVC % predicted at baseline above 75, wherein the benefit comprises a delay or prevention of the progression of skin fibrosis or a stabilization of the skin fibrosis as indicated in the mRSS. In addition, the dcSSc patients that have a FVC % predicted at baseline of 50-75 showed a smaller decline of lung function than expected. A higher decline of FVC is related to a lower probability of survival.

Within the meaning of the present invention, preventing or delaying of progression or stabilizing of dcSSc is measured as mRSS score and as FVC % predicted and is defined as a change of mRSS of −3 to 3 and as preventing a decrease of FVC % predicted of equal to or more than −10 from baseline to week 12-120, or from baseline to week 12-80, or from baseline to week 12-52, or from baseline to week 39-52, or from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured as mRSS score and as FVC % predicted and is defined as a change of mRSS of −3 to 3 and as preventing a decrease of FVC % predicted of equal to or more than −10 from baseline to week 12-52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured as mRSS score and as FVC % predicted and is defined as a change of mRSS of −3 to 3 and as preventing a decrease of FVC % predicted of equal to or more than −10 from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured by decreased number and severity of Raynaud's attacks across all Raynaud's categories measured; and reduction of development of new digital ulcers from baseline to week 12-120, or from baseline to week 12-80, or from baseline to week 12-52, or from baseline to week 39-52, or from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured by decreased number and severity of Raynaud's attacks across all Raynaud's categories measured; and reduction of development of new digital ulcers from baseline to week 12-52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, preventing or delaying of progression or stabilizing of dcSSc is measured by decreased number and severity of Raynaud's attacks across all Raynaud's categories measured; and reduction of development of new digital ulcers from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat).

Within the meaning of the present invention, methyl 4,6-diamino-2-[1-(2-fluorobenzyl)-1H-pyrazolo[3,4-b]pyridin-3-yl]-5-pyrimidinyl(methyl)carbamate (Riociguat) is given at a dose of 0.5 mg, 1 mg, 1.5 mg, 2 mg or 2.5 mg three times a day (TID).

Patients suffering from dcSSc and being ≥65 y of age, having a FVC % predicted at baseline of 50-75, and/or having a hsCRP>3 or a hsCRP>10 mg/L, respectively, showed not only a surprisingly pronounced treatment effect for the mean change of mRSS for Riociguat compared to placebo from baseline to week 52 of treatment with methyl 4,6-diamino-2-[1-(2-fluorobenzyl)-1H-pyrazolo[3,4-b]pyridin-3-yl]-5-pyrimidinyl(methyl)carbamate (Riociguat) but benefit in a higher degree than patients that being <65 y of age, having a FVC % predicted at baseline of >75, and/or having a hsCRP<3 or a hsCRP<10 mg/L. This pronounced treatment effect was shown as a mean change of mRSS for Riociguat compared to placebo of −6.7 units for patients ≥65 y of age, of −7.9 units for patients having a FVC % predicted at baseline of 50-75, of −5.8 units for patients having a hsCRP>3 and of −7.5 units for patients having a hsCRP>10 mg/L, respectively from baseline to week 52 of treatment with Riociguat.

Further embodiments of the present invention are as follows.

The treatment of patients suffering from dcSSc and being positive for at least one marker indicating an active disease with at least one sGC stimulator and/or sGC activator surprisingly resulted in a pronounced beneficial effect in the prevention or delay of disease progression or in the stabilization of the disease.

One embodiment of the invention is at least one sGC stimulator and/or sGC activator for use in a method of preventing or delaying disease progression and/or stabilizing of disease in patients suffering from diffuse cutaneous systemic sclerosis (dcSSc) and being positive for at least one marker indicating an active disease.

Within the meaning of the invention, the at least one marker indicating active disease is selected from the group consisting of the presence of anti-RNA polymerase III autoantibodies, of a hsCRP at baseline of >3 mg/L, and a FVC % predicted at baseline of 50-75.

One embodiment of the invention is at least one sGC stimulator and/or sGC activator for use in a method of preventing or delaying disease progression and/or stabilizing of disease in patients suffering from diffuse cutaneous systemic sclerosis (dcSSc) and being positive for at least one marker indicating an active disease, wherein the at least one marker indicating active disease is selected from the group consisting of the presence of anti-RNA polymerase III autoantibodies, i.e. patients being positive for anti-RNA polymerase III autoantibodies, a hsCRP at baseline of >3 mg/L, and a FVC % predicted at baseline of 50-75.

Another embodiment of the present invention is at least one sGC stimulator and/or sGC activator for use in a method of preventing or delaying disease progression and/or for stabilizing disease in patients suffering from dcSSc and being positive for anti-RNA polymerase III autoantibodies.

Another embodiment of the present invention is at least one sGC stimulator and/or sGC activator for use in a method of preventing or delaying disease progression and/or for stabilizing disease in patients suffering from dcSSc and having a FVC % predicted at baseline of 50-75.

Another embodiment of the present invention is at least one sGC stimulator and/or sGC activator for use in a method of preventing or delaying disease progression and/or for stabilizing disease in patients suffering from dcSSc and having a hsCRP at baseline of >3 mg/L.

Another embodiment of the present invention is at least one sGC stimulator and/or sGC activator for use in a method of preventing or delaying disease progression and/or for stabilizing disease in patients suffering from dcSSc and having a hsCRP at baseline of >10 mg/L.

Another embodiment of the present invention is at least one sGC stimulator and/or sGC activator for use in a method of preventing or delaying disease progression and/or for stabilizing disease in patients suffering from dcSSc and being positive for anti-RNA polymerase III autoantibodies and having a FVC % predicted at baseline of 50-75.

Another embodiment of the present invention is at least one sGC stimulator and/or sGC activator for use in a method of preventing or delaying disease progression and/or for stabilizing disease in patients suffering from dcSSc and being positive for anti-RNA polymerase III autoantibodies and having a hsCRP at baseline of >3 mg/L.

Another embodiment of the present invention is at least one sGC stimulator and/or sGC activator for use in a method of preventing or delaying disease progression and/or for stabilizing disease in patients suffering from dcSSc and being positive for anti-RNA polymerase III autoantibodies and having a hsCRP at baseline of >10 mg/L.

Another embodiment of the present invention is at least one sGC stimulator and/or sGC activator for use in a method of preventing or delaying disease progression and/or for stabilizing disease in patients suffering from dcSSc and having a FVC % predicted at baseline of 50-75 and having a hsCRP at baseline of >3 mg/L.

Another embodiment of the present invention is at least one sGC stimulator and/or sGC activator for use in a method of preventing or delaying disease progression and/or for stabilizing disease in patients suffering from dcSSc and having a FVC % predicted at baseline of 50-75 and having a hsCRP at baseline of >10 mg/L.

Another embodiment of the present invention is at least one sGC stimulator and/or sGC activator for use in a method of preventing or delaying disease progression and/or for stabilizing disease in patients suffering from dcSSc and being positive for anti-RNA polymerase III autoantibodies and having a FVC % predicted at baseline of 50-75 and having a hsCRP at baseline of >3 mg/L.

Another embodiment of the present invention is at least one sGC stimulator and/or sGC activator for use in a method of preventing or delaying disease progression and/or for stabilizing disease in patients suffering from dcSSc and being positive for anti-RNA polymerase III autoantibodies and having a FVC % predicted at baseline of 50-75 and having a hsCRP at baseline of >10 mg/L.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying disease progression and/or stabilizing of disease is defined as delaying or preventing progression or stabilizing of one or more of skin fibrosis, of dcSSc, concomitant fibrosis of internal organs, comprising the lung, the kidney, the heart, and the blood vessels, and of improving, i.e. decreasing, the score of the HAQ-DI.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of skin fibrosis is measured as mRSS score, wherein preventing or delaying disease progression is defined as preventing an increase of the mRSS of ≥4 units from baseline to week 12-120, or from baseline to week 12-60, or from baseline to week 12-52, or from baseline to week 39-52, or from baseline to week 52, and stabilizing the disease is defined as a change of the mRSS of −3 to 3 from baseline to week 12-120, or from baseline to week 12-80, or from baseline to week 12-52, or from baseline to week 39-52, or from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of skin fibrosis is measured as mRSS score, wherein preventing or delaying disease progression is defined as preventing an increase of the mRSS of ≥4 units from baseline to week 12-52, and stabilizing the disease is defined as a change of the mRSS of −3 to 3 from baseline to week 12-52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of skin fibrosis is measured as mRSS score, wherein preventing or delaying disease progression is defined as preventing an increase of the mRSS of ≥4 units from baseline to week 52, and stabilizing the disease is defined as a change of the mRSS of −3 to 3 from baseline to week 52 of treatment with at least one sGC stimulator and/or sGC activator.

A change of mRSS −3 to 3 from baseline to week 12-120, or from baseline to week 12-80, or from baseline to week 12-52, or from baseline to week 39-52, or from baseline to week 52 of treatment with at least one sGC stimulator and/or sGC activator is defined as almost no change of the mRSS.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 12-120, or from baseline to week 12-80, or from baseline to week 12-52, or from baseline to week 39-52, or from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 12-52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 52 of treatment with at least one sGC stimulator and/or sGC activator.

Within the meaning of the present invention, the term "preventing or delaying a decrease in FVC % predicted of equal to or more than −10 from baseline to a defined time or time range [weeks] of treatment with at least one sGC stimulator and/or sGC activator" has the meaning that the lung function as measured by FVC % predicted does not decrease or decline by more than 10% from baseline to the defined time or time range [weeks] of treatment with at least one sGC stimulator and/or sGC activator.

Within the meaning of the present invention, the term "preventing or delaying a decrease in FVC % predicted of equal to or more than −10 from baseline to a defined time or time range [weeks] of treatment with at least one sGC stimulator and/or sGC activator" has the meaning that the lung function as measured by FVC % predicted does not decrease or decline by more than 10% from baseline to the defined time or time range [weeks] of treatment with at least one sGC stimulator and/or sGC activator.

Within the meaning of the present invention, the terms decrease and decline of FVC % predicted are used synonymously.

In other words, if a patient has a FVC % predicted at baseline of 75, the term "preventing or delaying a decrease in FVC % predicted of equal to or more than −10 from baseline to a defined time or time range [weeks] of treatment with at least one sGC stimulator and/or sGC activator" has the meaning that the lung function of this patient as measured by FVC % predicted does not decrease or decline to 65 or less from baseline to the defined time or time range [weeks] of treatment with at least one sGC stimulator and/or sGC activator.

In other words, if a patient has a FVC % predicted at baseline of 75, the term "preventing a decrease in FVC % predicted of equal to or more than −10 from baseline to a defined time or time range [weeks] of treatment with at least one sGC stimulator and/or sGC activator" has the meaning that the lung function of this patient as measured by FVC % predicted will be more than 65 at the defined time or time range [weeks] of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured by HAQ-DI, wherein preventing or delaying disease progression and/or stabilizing disease is defined as a decrease in HAQ-DI of more than −0.21 from baseline to week 12-120, or from baseline to week 12-80, or from baseline to week 12-52, or from baseline to week 39-52, or from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured by HAQ-DI, wherein preventing or delaying disease progression and/or stabilizing disease is defined as a decrease in HAQ-DI of more than −0.21 from baseline to week 12-52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured by HAQ-DI, wherein preventing or delaying disease progression and/or stabilizing disease is defined as a decrease in HAQ-DI of more than −0.21 from baseline to week 52 of treatment with at least one sGC stimulator and/or sGC activator.

Within the meaning of the present invention, the terms decrease and decline in HAQ-DI are used synonymously.

Within the meaning of the present invention, the term "decrease in HAQ-DI of more than −0.21 from baseline to a defined time or time range [weeks] of treatment with at least one sGC stimulator and/or sGC activator" has the meaning that the HAQ-DI decreases or declines by more than −0.21 from baseline to the defined time or time range [weeks] of treatment with at least one sGC stimulator and/or sGC activator.

Within the meaning of the present invention, the term "decrease in HAQ-DI of more than −0.21 from baseline to a defined time or time range [weeks] of treatment with at least one sGC stimulator and/or sGC activator" has the meaning that the HAQ-DI decreases or declines by more than −0.21 from baseline to the defined time or time range [weeks] of treatment with at least one sGC stimulator and/or sGC activator.

In other words, if a patient has a HAQ-DI at baseline of 0.970, the term "decrease in HAQ-DI of more than −0.21 from baseline to a defined time or time range [weeks] of treatment with at least one sGC stimulator and/or sGC activator" has the meaning that the HAQ-DI of this patient decreases or declines to a value of below 0.760 from baseline to the defined time or time range [weeks] of treatment with at least one sGC stimulator and/or sGC activator.

dcSSc patients that are positive for anti-RNA polymerase III autoantibodies and which are known for a particularly aggressive disease progression early in the disease, surprisingly benefit significantly from a treatment with Riociguat, wherein the benefit comprises a delay or prevention of the progression of skin fibrosis and/or a stabilization of the skin fibrosis as indicated in the mRSS. In addition, fewer dcSSc patients that are positive for anti-RNA polymerase III autoantibodies showed a decrease of lung function (measured as FVC % predicted) of equal to or more than −10% from baseline to week 52 of treatment with Riociguat (−10% under Riociguat treatment vs −15.4% under placebo, respectively). No decline of lung function (FVC % predicted) was seen in the Riociguat group (+1.2) at week 52 compared to baseline and a worsening of the FVC % predicted in the placebo group (−3.7). A higher decline of FVC is related to a lower probability of survival.

This result could not be expected, as it is for example in contrast to the results of a Phase 2 study on Tocilizumab (fasSScinate), where the anti-RNA polymerase III autoantibody profile had little clinically meaningful influence on the effect of Tocilizumab on change in mRSS or ppFVC at week 48 (Lopez et al. 2018).

The present invention also shows that dcSSc patients that have a FVC % predicted at baseline of 50-75 and which are known for a lower probability of survival, surprisingly benefit significantly from a treatment with Riociguat, wherein the benefit comprises a delay or prevention of the progression of skin fibrosis or a stabilization of the skin fibrosis as indicated in the mRSS. In addition, the dcSSc patients that have a FVC % predicted at baseline of 50-75 showed a smaller decline of lung function than expected. A higher decline of FVC is related to a lower probability of survival.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured as mRSS score and as FVC % predicted and is defined as a change of mRSS of –3 to 3 and as preventing a decrease of FVC % predicted of equal to or more than –10 from baseline to week 12-120, or from baseline to week 12-80, or from baseline to week 12-52, or from baseline to week 39-52, or from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured as mRSS score and as FVC % predicted and is defined as a change of mRSS of –3 to 3 and as preventing a decrease of FVC % predicted of equal to or more than –10 from baseline to week 12-52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured as mRSS score and as FVC % predicted and is defined as a change of mRSS of –3 to 3 and as preventing a decrease of FVC % predicted of equal to or more than –10 from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured by decreased number and severity of Raynaud's attacks across all Raynaud's categories measured; and reduction of development of new digital ulcers from baseline to week 12-120, or from baseline to week 12-80, or from baseline to week 12-52, or from baseline to week 39-52, or from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured by decreased number and severity of Raynaud's attacks across all Raynaud's categories measured; and reduction of development of new digital ulcers from baseline to week 12-52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein preventing or delaying of progression or stabilizing of dcSSc is measured by decreased number and severity of Raynaud's attacks across all Raynaud's categories measured; and reduction of development of new digital ulcers from baseline to week 52 of treatment with at least one sGC stimulator and/or sGC activator.

Another embodiment of the present invention is at least one sGC stimulator and/or sGC activator for use in a method of preventing or delaying disease progression and/or for stabilizing disease in patients suffering from dcSSc and being positive for at least one marker indicating an active disease, wherein the at least one sGC stimulator and/or activator is given at a dose of 0.5 mg, 1 mg, 1.5 mg, 2 mg or 2.5 mg three times a day (TID).

Patients suffering from dcSSc and being ≥65 y of age, having a FVC % predicted at baseline of 50-75, and/or having a hsCRP>3 or a hsCRP>10 mg/L, respectively, showed a surprisingly pronounced treatment effect for the mean change of mRSS for Riociguat compared to placebo from baseline to week 52 of treatment with at least one sGC stimulator and/or sGC activator. This pronounced treatment effect was shown as a mean change of mRSS for Riociguat compared to placebo of –6.7 units for patients ≥65 y of age, of –7.9 units for patients having a FVC % predicted at baseline of 50-75, of –5.8 units for patients having a hsCRP>3 and of –7.5 units for patients having a hsCRP>10 mg/L, respectively from baseline to week 52 of treatment with Riociguat.

One embodiment of the invention is at least one sGC stimulator for use in a method of preventing or delaying disease progression or for use in a method of stabilizing disease in patients suffering from dcSSc and being positive for at least one marker indicating an active disease, wherein the at least on sGC stimulator is selected from the group consisting of:

2-[1-(2-fluorobenzyl)-1H-pyrazolo[3,4-b]pyridin-3-yl]-5-(4-morpholinyl)-4,6-pyrimidinediamine 2-[1-(2-fluorobenzyl)-1H-pyrazolo[3,4-b]pyridin-3-yl]-5-(4-pyridinyl)-4-pyrimidineamine methyl 4,6-diamino-2-[1-(2-fluorobenzyl)-1H-pyrazolo[3,4-b]pyridin-3-yl]-5-pyrimidinyl(methyl)carbamate (Riociguat, known from WO 03/095451, example 8)

methyl 4,6-diamino-2-[1-(2-fluorobenzyl)-1H-pyrazolo[3,4-b]pyridin-3-yl]-5-pyrimidinylcarbamate (Nelociguat, known from WO 03/095451, example 5)

methyl {4,6-diamino-2-[5-fluoro-1-(2-fluorobenzyl)-1H-pyrazolo[3,4-b]pyridine-3-yl]pyrimidin-5-yl}carbamate (Vericiguat, known from WO 2011/147809, example 1)

methyl {4,6-diamino-2-[5-fluoro-1-(2-fluorobenzyl)-1H-pyrazolo[3,4-b]pyridine-3-yl]pyrimidin-5-yl}methylcarbamate methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate 4-amino-2-[5-chloro-3(3,3,3-trifluoropropyl)-1H-indazol-1-yl]-5,5-dimethyl-5,7-dihydro-6H-pyrrolo[2,3-d]pyrimidin-6-one 4-amino-2[5-chloro-3-(2,3,6-trifluorobenzyl)-1H-indazol-1-yl]-5,5-dimethyl-5,7-dihydro-6H-pyrrolo[2,3-d]pyrimidin-6-one 4-amino-5,5-dimethyl-2-[3-(2,3,6-trifluorobenzyl)1H-thieno[3,4-c]pyrazol-1-yl]-5,7-dihydro-6H-pyrrolo[2,3-d]pyrimidin-6-one 4-amino-5,5-dimethyl-2-[3-(2,3,6-trifluorobenzyl)-1H-thieno[2,3-d]pyrazol-1-yl]-5,5-dimethyl-5,7-dihydro-6H-pyrrolo[2,3-d]pyrimidin-6-one 4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one 4-amino-2-[6-chloro-3-(2,3,6-trifluorobenzyl)imidazo[1,5-a]pyridin-1-yl]]-5,5-dimethyl-5,7-dihydro-6H-pyrrolo[2,3-d]pyrimidin-6-one 4-amino-2-[6-fluoro-3-(2,3,6-trifluorobenzyl)imidazo[1,5-a]pyridin-1-yl]]-5,5-dimethyl-5,7-dihydro-6H-pyrrolo[2,3-d]pyrimidin-6-one 4-amino-2-[6-fluoro-3-(2,3,6-trifluorobenzyl)6-fluoroimidazo[1,5-a]pyridin-1-yl]-5,5-dimethyl-5,7-dihydro-6H-pyrrolo[2,3-d]pyrimidin-6-one 4-amino-5,5-dimethyl-2-[3-(2,4,6-trifluorobenzyl)imidazo[1,5-a]pyridin-1-yl]-5,7-dihydro-6H-pyrrolo[2,3-d]pyrimidin-6-one 4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one 3-(4-amino-5-cyclopropylpyrimidin-2-yl)-1-(2-fluorobenzyl)-1H-pyrazolo[3,4-b]pyridine 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one (known from WO 2014/131760, example 2)

ent-N-[(2S)-amino-2-methylbutyl]-8-[(2,6-difluorobenzyl)oxy]-2,6-dimethylimidazo[1,2-a]pyridine-3-carboxamide (enantiomer A, known from WO 2014/068099, example 200)

ent-N-(2-amino-2-methylbutyl)-8-[(2,6-difluorobenzyl)oxy]-2,6-dimethylimidazo[1,2-a]pyridine-3-carboxamide (enantiomer B, known from WO 2014/068099, example 201)

ent-N-(2-amino-5,5,5-trifluoro-2-methylpentyl)-2,6-dimethyl-8-[(2,3,6-trifluorobenzyl)oxy]imidazo[1,2-a]pyridine-3-carboxamide (enantiomer B)

ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B, known from WO 2014/068099, example 409)

ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer A, known from WO 2014/068099, example 408)

ent-N-(2-amino-3-fluoro-2-methylpropyl)-2,6-dimethyl-8-[(2,3,6-trifluorobenzyl)oxy]imidazo[1,2-a]pyridine-3-carboxamide (enantiomer B)

ent-N-(2-amino-3-fluoro-2-methylpropyl)-8-[(2,6-difluorobenzyl)oxy]-2,6-dimethylimidazo[1,2-a]pyridine-3-carboxamide (enantiomer B)

ent-N-(2-amino-3-fluoro-2-methylpropyl)-8-[(2,6-difluorobenzyl)oxy]-2,6-dimethylimidazo[1,2-a]pyridine-3-carboxamide (enantiomer A)

rac-N-(2-amino-3-fluoro-2-methylpropyl)-8-[(2,6-difluorobenzyl)oxy]-2,6-dimethylimidazo[1,2-a]pyridine-3-carboxamide formate ent-N-(2-amino-3-fluoro-2-methylpropyl)-2,6-dimethyl-8-[(2,3,6-trifluorobenzyl)oxy]imidazo[1,2-a]pyridine-3-carboxamide (enantiomer A)

ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (enantiomer B)

ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (enantiomer A)

ent-N-(2-amino-3-fluoro-2-methylpropyl)-8-[(2,6-difluorobenzyl)oxy]-6-(fluoromethyl)-2-methylimidazo[1,2-a]pyridine-3-carboxamide 1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat)

5-fluoro-2-[1-(2-fluorobenzyl)-5-(1,2-oxazol-3-yl)-1H-pyrazol-3-yl]pyrimidin-4-ol (IWP-051)

IWP-121, IWP-427, IWP-953, IW-1701, and IW-6463, or a pharmaceutically acceptable salt thereof.

According to a further embodiment of the present invention, sGC stimulators for use according to the invention are selected from the group consisting of:

2-[1-(2-fluorobenzyl)-1H-pyrazolo[3,4-b]pyridin-3-yl]-5-(4-morpholinyl)-4,6-pyrimidinediamine 2-[1-(2-fluorobenzyl)-1H-pyrazolo[3,4-b]pyridin-3-yl]-5-(4-pyridinyl)-4-pyrimidineamine methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A).

ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B, known from WO 2014/068099, example 409)

ent-N-(2-amino-2-methylbutyl)-8-[(2,6-difluorobenzyl)oxy]-2,6-dimethylimidazo[1,2-a]pyridine-3-carboxamide (enantiomer B)

methyl {4,6-diamino-2-[5-fluoro-1-(2-fluorobenzyl)-1H-pyrazolo[3,4-b]pyridin-3-yl]pyrimidin-5-yl}methylcarbamate methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate 4-amino-2-[5-chloro-3(3,3,3-trifluoropropyl)-1H-indazol-1-yl]-5,5-dimethyl-5,7-dihydro-6H-pyrrolo[2,3-d]pyrimidin-6-one 4-amino-2[5-chloro-3-(2,3,6-trifluorobenzyl)-1H-indazol-1-yl]-5,5-dimethyl-5,7-dihydro-6H-pyrrolo[2,3-d]pyrimidin-6-one 4-amino-5,5-dimethyl-2-[3-(2,3,6-trifluorobenzyl)1H-thieno[3,4-c]pyrazol-1-yl]-5,7-dihydro-6H-pyrrolo[2,3-d]pyrimidin-6-one 4-amino-5,5-dimethyl-2-[3-(2,3,6-trifluorobenzyl)-1H-thieno[2,3-d]pyrazol-1-yl]-5,5-dimethyl-5,7-dihydro-6H-pyrrolo[2,3-d]pyrimidin-6-one 4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one 4-amino-2-[6-chloro-3-(2,3,6-trifluorobenzyl)imidazo[1,5-a]pyridin-1-yl]]-5,5-dimethyl-5,7-dihydro-6H-pyrrolo[2,3-d]pyrimidin-6-one 4-amino-2-[6-fluoro-3-(2,3,6-trifluorobenzyl)imidazo[1,5-a]pyridin-1-yl]]-5,5-dimethyl-5,7-dihydro-6H-pyrrolo[2,3-d]pyrimidin-6-one 4-amino-2-[6-fluoro-3-(2,3,6-trifluorobenzyl)6-fluoroimidazo[1,5-a]pyridin-1-yl]-5,5-dimethyl-5,7-dihydro-6H-pyrrolo[2,3-d]pyrimidin-6-one 4-amino-5,5-dimethyl-2-[3-(2,4,6-trifluorobenzyl)imidazo[1,5-a]pyridin-1-yl]]-5,7-dihydro-6H-pyrrolo[2,3-d]pyrimidin-6-one 4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one 3-(4-amino-5-cyclopropylpyrimidin-2-yl)-1-(2-fluorobenzyl)-1H-pyrazolo[3,4-b]pyridine 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and 1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, sGC stimulators for use according to the invention are selected from the group consisting of:

2-[1-(2-fluorobenzyl)-1H-pyrazolo[3,4-b]pyridin-3-yl]-5-(4-morpholinyl)-4,6-pyrimidinediamine 2-[1-(2-fluorobenzyl)-1H-pyrazolo[3,4-b]pyridin-3-yl]-5-(4-pyridinyl)-4-pyrimidineamine methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A)

ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B, known from WO 2014/068099, example 409)

ent-N-(2-amino-2-methylbutyl)-8-[(2,6-difluorobenzyl)oxy]-2,6-dimethylimidazo[1,2-a]pyridine-3-carboxamide (enantiomer B)

methyl {4,6-diamino-2-[5-fluoro-1-(2-fluorobenzyl)-1H-pyrazolo[3,4-b]pyridine-3-yl]pyrimidin-5-yl}methylcarbamate 3-(4-amino-5-cyclopropylpyrimidin-2-yl)-1-(2-fluorobenzyl)-1H-pyrazolo[3,4-b]pyridine 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and 1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, sGC stimulators for use according to the invention are selected from the group consisting of:

methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A)

ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B, known from WO 2014/068099, example 409)

1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, sGC stimulators for use according to the invention are selected from the group consisting of:

methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A).

1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof.

According to a further embodiment of the present invention, the sGC stimulator for use according to the invention is:

methyl 4,6-diamino-2-[1-(2-fluorobenzyl)-1H-pyrazolo[3,4-b]pyridin-3-yl]-5-pyrimidinyl(methyl)carbamate (Riociguat) or a pharmaceutically acceptable salt thereof.

According to a further embodiment of the present invention, the sGC stimulator for use according to the invention is:

methyl {4,6-diamino-2-[5-fluoro-1-(2-fluorobenzyl)-1H-pyrazolo[3,4-b]pyridine-3-yl]pyrimidin-5-yl}carbamate (Vericiguat) or a pharmaceutically acceptable salt thereof.

According to a further embodiment of the present invention, the sGC stimulator for use according to the invention is:

ent-N-[(2S)-amino-2-methylbutyl]-8-[(2,6-difluorobenzyl)oxy]-2,6-dimethylimidazo[1,2-a]pyridine-3-carboxamide (enantiomer A) or a pharmaceutically acceptable salt thereof.

According to a further embodiment of the present invention, the sGC activator for use according to the invention is selected from the group consisting of:

4-({(4-carboxybutyl) [2-(2-{[4-(2-phenylethyl)benzyl]oxy}phenyl)ethyl]amino}methyl)benzoic acid 4-({(4-carboxybutyl)[2-(5-fluoro-2-{[4'-(trifluoromethyl) [1,1'-biphenyl]-4-yl]methoxy}phenyl)ethyl] amino}methyl)benzoic acid (BAY 60-2770)

5-chloro-2-(5-chlorothiophene-2-sulfonylamino-N-(4-(morpholine-4-sulfonyl)phenyl)benzamide as sodium salt 2-(4-chlorophenylsulfonylamino)-4,5-dimethoxy-N-(4-(thiomorpholine-4-sulfonyl)phenyl)benzamide 1-{6-[5-chloro-2-({4-trans-4-}trifluoromethyl)cyclohexyl] benzyl}oxy)phenyl]pyridin-2-yl}-5-(trifluoromethyl)-1H-pyrazole-4-carboxylic acid 1-[6-(2-(2-methyl-4-(4-trifluoromethoxyphenyl)benzyloxy) phenyl)pyridin-2-yl]-5-trifluoromethylpyrazole-4-carboxylic acid 1[6-(3,4-dichlorophenyl)-2-pyridinyl-5-(trifluoromethyl)-1H-pyrazole-4-carboxylic acid 1-({2-[3-chloro-5-(trifluoromethyl)phenyl]-5-methyl-1,3-thiazol-4-yl}methyl)-1H-pyrazole-4-carboxylic acid 4-({2-[3-(trifluoromethyl)phenyl]-1,3-thiazol-4-yl}methyl) benzoic acid 1-({2-[2-fluoro-3-(trifluoromethyl)phenyl]-5-methyl-1,3-thiazol-4-yl}methyl)-1H-pyrazole-4-carboxylic acid 3-(4-chloro-3-{[(2S,3R)-2-(4-chlorophenyl)-4,4,4-trifluoro-3-methylbutanoyl]amino}phenyl)-3-cyclopropylpropanoic acid (known from WO 2012/139888, example 22)

5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid (known from WO 2014/012934, example 23)

5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid (known from WO 2014/012934, example 7)

(1R,5 S)-3-[4-(5-methyl-2-{[2-methyl-4-(piperidin-1-ylcarbonyl)benzyl]oxy}phenyl)-1,3-thiazol-2-yl]-3-azabicyclo[3.2.1]octane-8-carboxylic acid and 1-[6-(5-methyl-2-{[2-(tetrahydro-2H-pyran-4-yl)-1,2,3,4-tetrahydroisoquinolin-6-yl]methoxy}phenyl)pyridin-2-yl]-5-(trifluoromethyl)-1H-pyrazole-4-carboxylic acid, or a pharmaceutically acceptable salt thereof.

According to a further embodiment of the present invention, the sGC activator for use according to the invention is selected from the group consisting of:

3-(4-chloro-3-{[(2S,3R)-2-(4-chlorophenyl)-4,4,4-trifluoro-3-methylbutanoyl]amino}phenyl)-3-cyclopropylpropanoic acid 4-({(4-carboxybutyl) [2-(5-fluoro-2-{[4'-(trifluoromethyl) [1,1'-biphenyl]-4-yl]methoxy}phenyl)ethyl] amino}methyl)benzoic acid 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid and 5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid, or a pharmaceutically acceptable salt thereof.

According to a further embodiment of the present invention, the sGC activator for use according to the invention is:

3-(4-chloro-3-{[(2S,3R)-2-(4-chlorophenyl)-4,4,4-trifluoro-3-methylbutanoyl]amino}phenyl)-3-cyclopropylpropanoic acid or a pharmaceutically acceptable salt thereof.

According to a further embodiment of the present invention, the sGC activator for use according to the invention is:

4-({(4-carboxybutyl) [2-(5-fluoro-2-{[4'-(trifluoromethyl) [1,1'-biphenyl]-4-yl]methoxy}phenyl)ethyl] amino}methyl)benzoic acid or a pharmaceutically acceptable salt thereof.

A further embodiment of the invention is at least one sGC activator selected from the group consisting of the compounds 3-(4-chloro-3-{[(2S,3R)-2-(4-chlorophenyl)-4,4,4-trifluoro-3-methylbutanoyl]amino}phenyl)-3-cyclopropylpropanoic acid, 4-({(4-carboxybutyl) [2-(5-fluoro-2-{[4'-(trifluoromethyl) [1,1'-biphenyl]-4-yl]methoxy}phenyl)ethyl] amino}methyl)benzoic acid, 5-{(4-carboxybutyl) [2-(2-{[3-chloro-4'-(trifluoromethyl) biphenyl-4-yl]methoxy}phenyl)ethyl]amino}-5,6,7,8-tetrahydroquinoline-2-carboxylic acid, and 5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid or a pharmaceutically acceptable salt thereof for use according to the invention.

Further sGC activators in the context of the invention are known from the following publications: WO2013/157528, WO2015/056663, WO2009/123316, WO2016/001875, WO2016/001876, WO2016/001878, WO2000/02851, WO2012/122340, WO2013/025425, WO2014/039434, WO2016/014463, WO2009/068652, WO2009/071504, WO2010/015652, WO2010/015653, WO2015/033307, WO2016/042536, WO2009/032249, WO2010/099054, WO2012/058132, US2010/0216764, WO2001/19776, WO2001/19780, WO2001/19778, WO2002/070459, WO2002/070460, WO2002/070510, WO2002/070462, WO2007/045366, WO2007/045369, WO2007/045433, WO2007/045370, WO2007/045367, WO2014/012935, WO2014/012934, WO2011/141409, WO2008/119457, WO2008/119458, WO2009/127338, WO2010/102717, WO2011/051165, WO2012/076466, WO2012/139888, WO2013/157528, WO2013/174736, WO2014/012934, WO2015/056663, WO2017103888, WO2017112617, WO2016042536, WO2016081668, WO2016191335, WO2016191334, WO2016001875, WO2016001876, WO2016001878, WO2016014463, WO2016044447, WO2016044445, WO2016044446, WO2015056663, WO2015033307, WO2015187470, WO2015088885, WO2015088886, WO2015089182, WO2014084312, WO2014039434, WO2014144100, WO2014047111, WO2014047325, WO2013025425, WO2013101830, WO2012165399, WO2012058132, WO2012122340, WO2012003405, WO2012064559, WO2011149921, WO2011119518, WO2011115804, WO2011056511, CN101670106, TW201028152, WO2010015653, WO2010015652, WO2010099054, WO2010065275, WO2009123316, WO2009068652, WO2009071504, WO2009032249, US2009209556.

A further embodiment of the invention is at least one sGC stimulator selected from one of the groups specified above or a pharmaceutically acceptable salt thereof for use according to the invention, wherein the at least one sGC stimulator or a pharmaceutically acceptable salt thereof is administered at a dose of 0.5 mg, 1 mg, 1.5 mg, 2 mg, or 2.5 mg three times a day.

The compounds according to the invention can be used alone or in combination with other active substances if necessary. The present invention further relates to medicinal products containing at least one of the compounds according to the invention and one or more further active substances, in particular for the treatment of the aforementioned diseases. Active substances that are particularly suitable for combinations are for example and preferably:

organic nitrates and NO-donors, for example sodium nitroprusside, nitroglycerin, isosorbide mononitrate, isosorbide dinitrate, molsidomine or SIN-1, and inhalational NO;

other vasoactive drugs, for examples prostanoids, such as iloprost, beraprost, cicaprost, epoprostenol, treprostinil;

other vasoactive drugs, for example Rho-kinase inhibitors such as fasudil;

other vasoactive drugs, for example endothelin receptor antagonists such as bosentan, darusentan, ambrisentan or sitaxsentan, macitentan;

active substances for lowering blood pressure, for example and preferably from the group of calcium antagonists, such as nifedipine, amlodipine, verapamil or diltiazem;

active substances for lowering blood pressure, for example and preferably from the group of angiotensin AII antagonists, ACE inhibitors, renin inhibitors, alpha-blockers, beta-blockers, mineralocorticoid receptor antagonists and diuretics; and/or antithrombotic agents, for example and preferably from the group of platelet aggregation inhibitors, anticoagulants, thrombin inhibitors or profibrinolytic substances;

active substances that alter fat metabolism, for example and preferably from the group of thyroid receptor agonists, cholesterol synthesis inhibitors such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists;

active substances that are used in fibrotic disorders, for examples and preferable from the group of protein kinase inhibitors such as sorafenib, regorafenib, imatinib, dasatinib, nilotinib nintedanib, bortezomib and/or pirfenidone;

active substances that alter inflammatory responses and/or supress immune responses, for example but not restricted to systemically or inhalatively administered corticosteroids, flutiform, acetylcysteine, mycophenolate mofetil (MMF), cyclophosphamide (CYC), methotrexate (MTX), rapamycin, azathioprin, tocilizumab, infliximab, rituximab, adalimumab, belimumab, abatacept, SAR100842, IVA337, bardoxolone methyl, lenabasum, thalidomide derivates;

active substances additionally working on different pathways, for example pirfenidone, nintedanib (BIBF-1120), SAR100842, thalidomide derivatives, integrin inhibitors.

sGC Stimulators selected from methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A) and 1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), sGC Activators selected from 3-(4-chloro-3-{[(2S,3R)-2-(4-chlorophenyl)-4,4,4-trifluoro-3-methylbutanoyl]amino}phenyl)-3-cyclopropylpropanoic acid 4-({(4-carboxybutyl)[2-(5-fluoro-2-{[4'-(trifluoromethyl)[1,1'-biphenyl]-4-yl]methoxy}phenyl)ethyl]amino}methyl)benzoic acid 5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid and 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid sGC modulator selected from the group consisting of IW-1973, IW-3718, IW-6463, (2R)-3,3,3-trifluoro-2-{[(5-fluoro-2-{1-[(2-fluorophenyl)methyl]-5-(1,2-oxazol-3-yl)-1H-pyrazol-3-yl}pyrimidin-4-yl)amino]methyl}-2-hydroxypropanamide (Olinciguat, IW-1701), and (1R,5S,8s)-3-(4-(5-methyl-2-((2-methyl-4-(piperidine-1-carbonyl)benzyl)oxy)phenyl)thiazol-2-yl)-3-azabicyclo[3.2.1]octane-8-carboxylic acid (BI-703704).

The combinations described in the present invention are therefore effective for controlling dcSSc with unexpected beneficial properties compared to the state of the art.

A further embodiment of the invention is a combination of at least one sGC stimulator and/or activator selected from one of the groups specified above or a pharmaceutically acceptable salt thereof and at least one compound selected from the group consisting of methotrexate, mycophenolate mofetil, cyclophosphamide, azathioprine, and systemically or inhalatively administered corticosteroids for use in the treatment of dcSSC in a mammal in need of such treatment.

A further embodiment of the invention is a combination of the sGC stimulators methyl 4,6-diamino-2-[1-(2-fluorobenzyl)-1H-pyrazolo[3,4-b]pyridin-3-yl]-5-pyrimidinyl(methyl)carbamate (Riociguat)

methyl 4,6-diamino-2-[1-(2-fluorobenzyl)-1H-pyrazolo[3,4-b]pyridin-3-yl]-5-pyrimidinylcarbamate (Nelociguat)

methyl {4,6-diamino-2-[5-fluoro-1-(2-fluorobenzyl)-1H-pyrazolo[3,4-b]pyridine-3-yl]pyrimidin-5-yl}carbamate (Vericiguat)

ent-N-[(2S)-amino-2-methylbutyl]-8-[(2,6-difluorobenzyl)oxy]-2,6-dimethylimidazo[1,2-a]pyridine-3-carboxamide (enantiomer A) and/or 1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat), or a pharmaceutically acceptable salt thereof and at least one compound selected from the group consisting of methotrexate, mycophenolate mofetil, cyclophosphamide, azathioprine, and systemically or inhalatively administered corticosteroids for use in a method of preventing or delaying disease progression and/or stabilizing of disease in patients suffering from diffuse cutaneous systemic sclerosis (dcSSc) and being positive for at least one marker indicating an active disease.

A further embodiment of the invention is a combination of the sGC activators 3-(4-chloro-3-{[(2S,3R)-2-(4-chlorophenyl)-4,4,4-trifluoro-3-methylbutanoyl]amino}phenyl)-3-cyclopropylpropanoic acid, 4-({(4-carboxybutyl) [2-(5-fluoro-2-{[4'-(trifluoromethyl)[1,1'-biphenyl]-4-yl]methoxy}phenyl)ethyl]amino}methyl)benzoic acid, 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid, and 5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid.

or a pharmaceutically acceptable salt thereof and at least one compound selected from the group consisting of methotrexate, mycophenolate mofetil, cyclophosphamide, azathioprine, and systemically or inhalatively administered corticosteroids for use in a method of preventing or delaying disease progression and/or stabilizing of disease in patients suffering from diffuse cutaneous systemic sclerosis (dcSSc) and being positive for at least one marker indicating an active disease.

A further embodiment of the invention is a medicament comprising at least one sGC stimulator and/or activator selected from one of the groups specified above or a pharmaceutically acceptable salt thereof or a combination as described above for use in a method of preventing or delaying disease progression and/or stabilizing of disease in patients suffering from diffuse cutaneous systemic sclerosis (dcSSc) and being positive for at least one marker indicating an active disease.

A further embodiment of the invention is a medicament comprising at least one sGC stimulator and/or activator selected from one of the groups specified above or a pharmaceutically acceptable salt thereof or a combination as described above for use in a method of preventing or delaying disease progression and/or stabilizing of disease in patients suffering from diffuse cutaneous systemic sclerosis (dcSSc) and being positive for anti-RNA polymerase III autoantibodies A further embodiment of the invention is a medicament comprising one or more sGC stimulator selected from the group consisting of
methyl 4,6-diamino-2-[1-(2-fluorobenzyl)-1H-pyrazolo[3,4-b]pyridin-3-yl]-5-pyrimidinyl(methyl)carbamate (Riociguat)
methyl 4,6-diamino-2-[1-(2-fluorobenzyl)-1H-pyrazolo[3,4-b]pyridin-3-yl]-5-pyrimidinylcarbamate (Nelociguat)
methyl {4,6-diamino-2-[5-fluoro-1-(2-fluorobenzyl)-1H-pyrazolo[3,4-b]pyridine-3-yl]pyrimidin-5-yl}carbamate (Vericiguat)
ent-N-[(2S)-amino-2-methylbutyl]-8-[(2,6-difluorobenzyl)oxy]-2,6-dimethylimidazo[1,2-a]pyridine-3-carboxamide (enantiomer A) and/or
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat),
or a pharmaceutically acceptable salt thereof
or a combination as described above for use in a method of preventing or delaying disease progression and/or stabilizing of disease in patients suffering from diffuse cutaneous systemic sclerosis (dcSSc) and being positive for at least one marker indicating an active disease.

A further embodiment of the invention is a medicament comprising one or more sGC stimulator selected from the group consisting of
methyl 4,6-diamino-2-[1-(2-fluorobenzyl)-1H-pyrazolo[3,4-b]pyridin-3-yl]-5-pyrimidinyl(methyl)carbamate (Riociguat)
methyl 4,6-diamino-2-[1-(2-fluorobenzyl)-1H-pyrazolo[3,4-b]pyridin-3-yl]-5-pyrimidinylcarbamate (Nelociguat)
methyl {4,6-diamino-2-[5-fluoro-1-(2-fluorobenzyl)-1H-pyrazolo[3,4-b]pyridine-3-yl]pyrimidin-5-yl}carbamate (Vericiguat)
ent-N-[(2S)-amino-2-methylbutyl]-8-[(2,6-difluorobenzyl)oxy]-2,6-dimethylimidazo[1,2-a]pyridine-3-carboxamide (enantiomer A) and/or
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat),
or a pharmaceutically acceptable salt thereof
or a combination as described above for use in a method of preventing or delaying disease progression and/or stabilizing of disease in patients suffering from diffuse cutaneous systemic sclerosis (dcSSc) and being positive for anti-RNA polymerase III autoantibodies.

A further embodiment of the invention is a medicament comprising Riociguat or a pharmaceutically acceptable salt thereof in a dose described above or a combination as described above for use in a method of preventing or delaying disease progression and/or stabilizing of disease in patients suffering from diffuse cutaneous systemic sclerosis (dcSSc) and being positive for at least one marker indicating an active disease.

A further embodiment of the invention is a medicament comprising Riociguat or a pharmaceutically acceptable salt thereof in a dose described above or a combination as described above for use in a method of preventing or delaying disease progression and/or stabilizing of disease in patients suffering from diffuse cutaneous systemic sclerosis (dcSSc) and being positive for anti-RNA polymerase III autoantibodies.

Further embodiments of the present invention are:
1. At least one sGC stimulator and/or sGC activator for use in a method of preventing or delaying disease progression and/or stabilizing of disease in patients suffering from diffuse cutaneous systemic sclerosis (dcSSc) and being positive for at least one marker indicating an active disease.
2. At least one sGC stimulator and/or sGC activator for use according to Embodiment 1, wherein the at least one marker indicating an active disease is selected from the group consisting of the presence of anti-RNA polymerase III autoantibodies, a hsCRP at baseline of >3 mg/L, and FVC % predicted at baseline of 50-75.
3. At least one sGC stimulator and/or sGC activator for use according to Embodiment 1 or 2, wherein the at least one marker indicating an active disease is the presence of anti-RNA polymerase III autoantibodies
4. At least one sGC stimulator and/or sGC activator for use according to Embodiment 1 or 2, wherein the at least one marker indicating an active disease is a FVC % predicted at baseline of 50-75.
5. At least one sGC stimulator and/or sGC activator for use according to Embodiment 1 or 2, wherein the at least one marker indicating an active disease is a hsCRP at baseline of >3 mg/L.
6. At least one sGC stimulator and/or sGC activator for use according to Embodiment 1 or 2, wherein the at least one marker indicating an active disease is the presence of anti-RNA polymerase III autoantibodies, a FVC % predicted at baseline of 50-75 and a hsCRP at baseline of >3 mg/L.
7. At least one sGC stimulator and/or sGC activator for use according to any of Embodiments 1 to 6, wherein preventing or delaying disease progression and/or stabilizing of disease is defined as delaying or preventing progression or stabilizing of one or more of skin fibrosis, of dcSSc concomitant fibrosis of internal organs, comprising the lung, the kidney, the heart, and the blood vessels, and of decreasing the score of the HAQ-DI.
8. At least one sGC stimulator and/or sGC activator for use according to any of Embodiments 1 to 7, wherein preventing or delaying of progression or stabilizing of skin fibrosis is measured as mRSS score, wherein preventing or delaying disease progression is defined as preventing an increase of the mRSS of ≥4 units from baseline to week 12-52, and stabilizing the disease is defined as a change of the mRSS of −3 to 3 from baseline to week 12-52 of treatment with at least one sGC stimulator and/or sGC activator.

9. At least one sGC stimulator and/or sGC activator for use according to any of Embodiments 1 to 7, wherein preventing or delaying of progression or stabilizing of dcSSc concomitant fibrosis of the lung is measured as FVC % predicted, wherein preventing or delaying disease progression and/or stabilizing disease is defined as preventing a decrease in FVC % predicted of equal to or more than −10 from baseline to week 12-52 of treatment with at least one sGC stimulator and/or sGC activator.

10. At least one sGC stimulator and/or sGC activator for use according to any of Embodiments 1 to 7, wherein preventing or delaying progression or stabilizing of dcSSc is measured by HAQ-DI, wherein preventing or delaying disease progression and/or stabilizing disease is defined as a decrease in HAQ-DI of more than −0.21 from baseline to week 12-52 of treatment with at least one sGC stimulator and/or sGC activator.

11. At least one sGC stimulator and/or sGC activator for use according to any of Embodiments 1 to 7, wherein preventing or delaying of progression or stabilizing of dcSSc is measured as mRSS score and as FVC % predicted and is defined as preventing an increase of the mRSS of ≥4 units or as a change of mRSS of −3 to 3 and as preventing a decrease of FVC % predicted of equal to or more than −10 from baseline to week 12-52 of treatment with at least one sGC stimulator and/or sGC activator.

12. At least one sGC stimulator and/or sGC activator for use according to Embodiments 1 to 7, wherein preventing or delaying of progression or stabilizing of dcSSc is measured by a decreased number and severity of Raynaud's attacks and a reduction of development of new digital ulcers from baseline to week 12-52 of treatment with at least one sGC stimulator and/or sGC activator.

13. At least one sGC stimulator and/or sGC activator for use according to any of Embodiments 1 to 12, wherein the sGC stimulator is selected from the group consisting of
methyl 4,6-diamino-2-[1-(2-fluorobenzyl)-1H-pyrazolo[3,4-b]pyridin-3-yl]-5-pyrimidinyl(methyl)carbamate (Riociguat),
methyl 4,6-diamino-2-[1-(2-fluorobenzyl)-1H-pyrazolo[3,4-b]pyridin-3-yl]-5-pyrimidinylcarbamate (Nelociguat),
methyl {4,6-diamino-2-[5-fluoro-1-(2-fluorobenzyl)-1H-pyrazolo[3,4-b]pyridine-3-yl]pyrimidin-5-yl}carbamate (Vericiguat),
ent-N-[(2S)-amino-2-methylbutyl]-8-[(2,6-difluorobenzyl)oxy]-2,6-dimethylimidazo[1,2-a]pyridine-3-carboxamide (enantiomer A) and
1,1,1,3,3,3-Hexafluoro-2-[({5-fluoro-2-[1-(2-fluorobenzyl)-5-(1,2-oxazol-3-yl)-1H-pyrazol-3-yl]-4-pyrimidinyl}amino)methyl]-2-propanol (Praliciguat),
or a pharmaceutically acceptable salt thereof.

14. At least one sGC stimulator and/or sGC activator for use according to Embodiment 13, wherein the at least one sGC stimulator is
methyl 4,6-diamino-2-[1-(2-fluorobenzyl)-1H-pyrazolo[3,4-b]pyridin-3-yl]-5-pyrimidinyl(methyl)carbamate (Riociguat),
or a pharmaceutically acceptable salt thereof.

15. Combination of at least one sGC stimulator and/or sGC activator and at least one compound selected from the group consisting of methotrexate, mycophenolate mofetil, cyclophosphamide, azathioprine, and systemically or inhalatively administered corticosteroids for use according to any of Embodiments 1 to 14.

FIGURE LEGENDS

FIG. 1: Forest plot for change in mRSS at week 52 for each subgroup. Difference in LSMeans=difference in least square means between Riociguat and placebo for each subgroup at week 52 of treatment with Riociguat or placebo.

Figure 2:
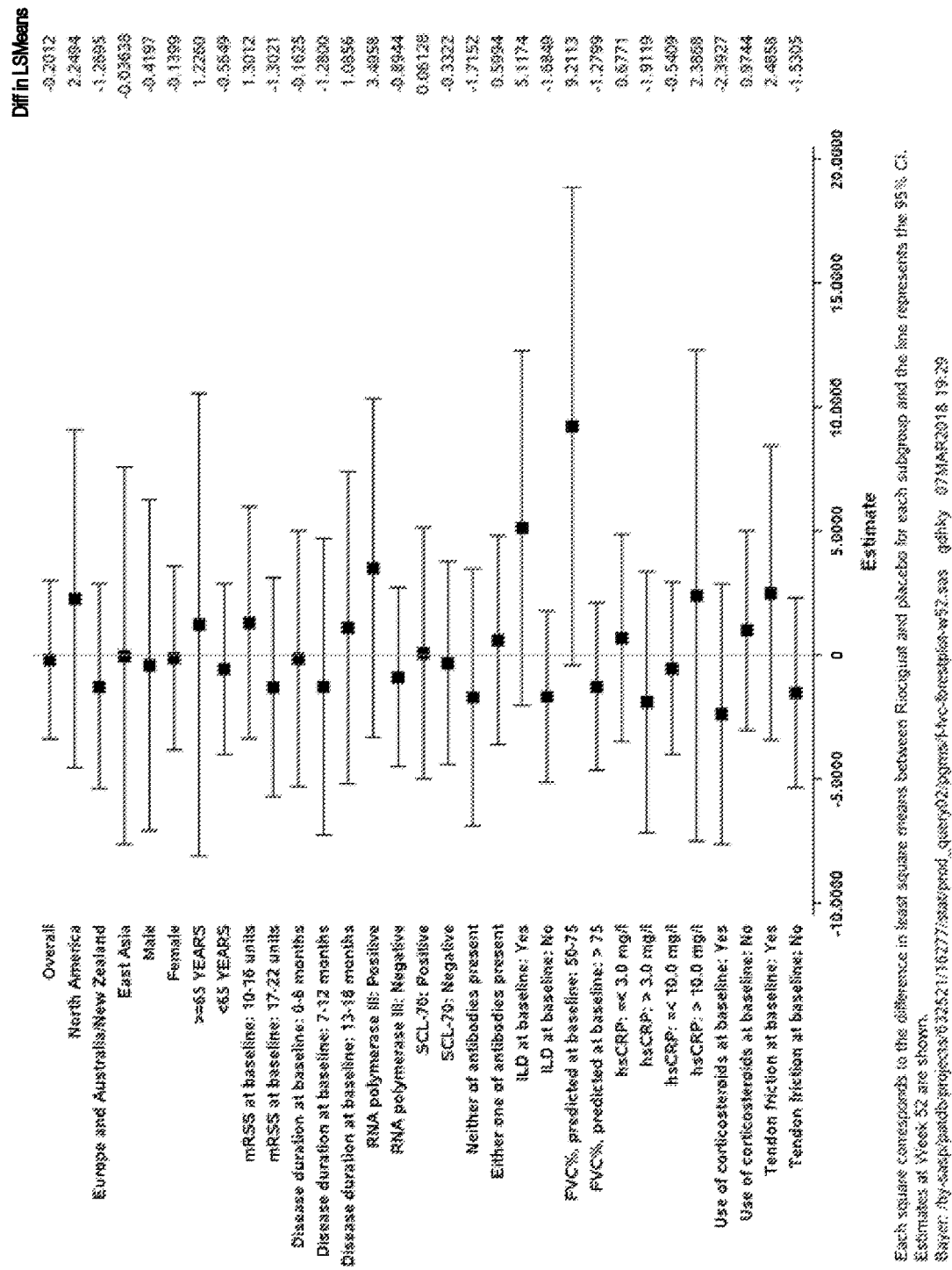

FIG. 2: Forest plot for change in FVC % predicted at week 52 for each subgroup. Difference in LSMeans=difference in least square means between Riociguat and placebo for each subgroup at week 52 of treatment with Riociguat or placebo.

Figure 3:
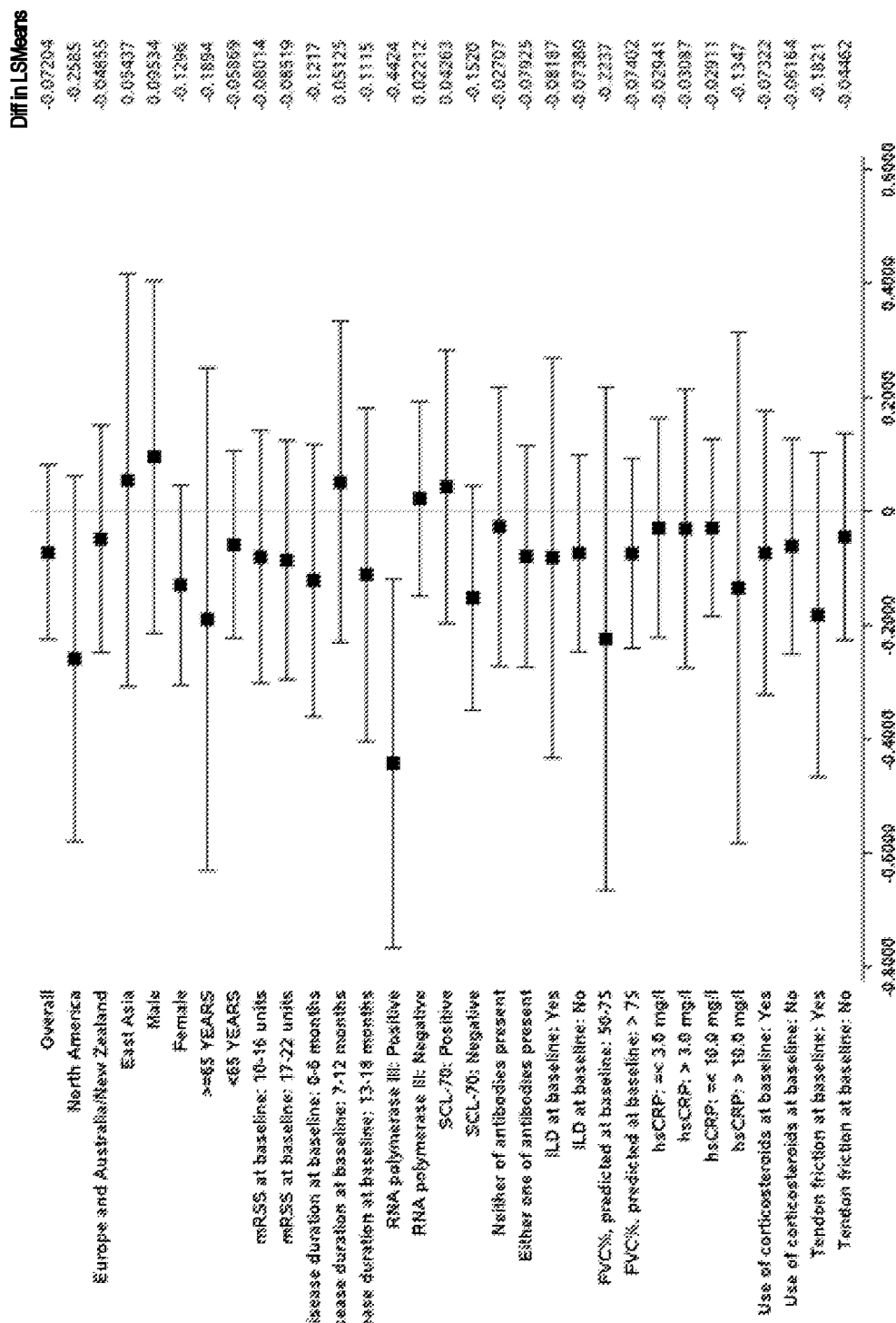

FIG. 3: Forest plot for change in HAQ-DI at week 52 for each subgroup. Difference in LSMeans=difference in least square means between Riociguat and placebo for each subgroup at week 52 of treatment with Riociguat or placebo.

A) Assessment of Physiological Efficacy/Clinical Study

A-1) Modified Rodnan Skin Score (mRSS)

The modified Rodnan skin score (mRSS) is a measure of skin thickness and is used as a primary or secondary outcome measure in clinical trials of systemic sclerosis. The maximum mRSS possible is 51. Standardization of the modified Rodnan skin score for use in clinical trials of systemic sclerosis is described in Khanna, D. et al., 2017b.

A-2) FVC % predicted

Pulmonary physiologic measures, particularly FVC, have frequently been used as surrogate endpoints for SSc-ILD and IPF. In SSc-ILD decline of FVC % predicted has been demonstrated to correlate with the extent and worsening of lung fibrosis (Khanna et al. 2015). Also in IPF measurable decline in FVC is correlated with mortality. To reflect progression of ILD and lung fibrosis, a decline of FVC % predicted equal to or more than −10 is used.

A-3) HAQ-DI

The Health Assessment Questionnaire Disability Index (HAQ-DI) is a well-accepted measure of physical function for various rheumatic diseases, and it is the most widely employed and reported measure for assessing physical function in SSc. As a post hoc analysis in study 16277, the percentage of patients stratified by HAQ-DI categorized change was also performed. Clinically meaningful disease improvement was defined as a decrease in HAQ-DI of more than −0.21 from baseline to week 52; stabilization and/or disease worsening were defined as a change in HAQ-DI less than or equal to −0.21 from baseline to week 52.

A-4) Clinical Study, RISE-SSc

The RISE-SSc study is a multinational randomized (1:1), double-blind, placebo controlled, parallel-group study, 121 patients were randomized between study arms (60 patients to the Riociguat group and 61 to the placebo group) (NCT02283762; https://clinicaltrials.gov/ct2/show/NCT02283762). The overall objectives of this study were to evaluate the efficacy and safety of 52 weeks of treatment with Riociguat versus placebo in patients with dcSSc. The study design consists of a placebo-controlled treatment phase followed by a long-term extension, as follows: a screening phase of up to 2 weeks followed by a 52-week double-blind main treatment phase where patients will be dose titrated over a 10-week period and maintained on therapy for up to 42 weeks; the open-label long-term extension phase will dose-titrate patients formerly on placebo onto Riociguat over a 10-week period and then maintain them on therapy for up to 42 weeks. The primary efficacy outcome measure was the change in mRSS from baseline to week 52. Key secondary efficacy measure was Combined Response Index for Systemic Sclerosis (CRISS). Secondary and exploratory efficacy measures included mRSS progression rate (defined as increase in mRSS by >5 units and ≥25% from baseline) and mRSS regression rate (defined as decrease in mRSS by >5 units and ≥25% from baseline); patient's and physician's global assessment; HRQoL using Medical Outcomes Study 36-item Short Form (SF-36) and the Scleroderma Health Assessment Questionnaire (SHAQ) (consisting of the HAQ Disability Index and 6 visual analog scales); digital ulcer count at each and overall ulcer burden (defined as total number of ulcers at a defined time point minus number of ulcers at baseline) and proportion of patients who do not develop new ulcers; change in FVC % predicted and DLCO % predicted; and need for escape therapy.

B) Results

TABLE 1

Change in mRSS at week 52 of the study for different patient subgroups, data taken from FIG. 1

| Patient Subgroup | | Difference in LSMeans*) with regard to mRSS |
|---|---|---|
| anti-RNA polymerase III autoantibodies | positive | −10.5 |
| | negative | 0.3 |
| FVC % predicted at baseline: | 50-75 | −8.0 |
| | >75 | −1.7 |
| hsCRP: | >3 mg/L | −5.8 |
| | ≤3 mg/L | 1.0 |
| hsCRP: | >10 mg/L | −7.5 |
| | ≤10 mg/L | −1.2 |

*)difference in LSMeans = difference in least square means between Riociguat and placebo for each subgroup at week 52 after start of the study.

TABLE 2

Change in FVC % predicted at week 52 of the study for different patient subgroups, data taken from FIG. 2

| Patient Subgroup | | Difference in LSMeans*) with regard to FVC % predicted |
|---|---|---|
| anti-RNA polymerase III autoantibodies | positive | 3.5 |
| | negative | −0.9 |
| FVC % predicted at baseline: | 50-75 | 9.2 |
| | >75 | −1.3 |
| ILD at baseline: | yes | 5.1 |
| | no | −1.7 |
| hsCRP: | >10 mg/L | 2.4 |
| | ≤10 mg/L | −0.5 |

*)difference in LSMeans = difference in least square means between Riociguat and placebo for each subgroup at week 52 after start of the study.

TABLE 3

Change in HAQ-DI at week 52 of the study for different patient subgroups, data taken from FIG. 3

| Patient Subgroup | | Difference in LSMeans*) with regard to HAQ-DI |
|---|---|---|
| anti-RNA polymerase III autoantibodies | positive | −0.44 |
| | negative | 0.02 |
| FVC % predicted at baseline: | 50-75 | −0.22 |
| | >75 | −0.07 |

TABLE 3-continued

Change in HAQ-DI at week 52 of the study for different patient subgroups, data taken from FIG. 3

| Patient Subgroup | | Difference in LSMeans*) with regard to HAQ-DI |
|---|---|---|
| hsCRP: | >10 mg/L | −0.13 |
| | ≤10 mg/L | −0.03 |

*)difference in LSMeans = difference in least square means between Riociguat and placebo for each subgroup at week 52 after start of the study.

REFERENCES

Beyer C, Reich N, Schindler S C, Akhmetshina A, Dees C, Tomcik M, Hirth-Dietrich C, von Degenfeld G, Sandner P, Distler O, Schett G, and Distler J H (2012). Stimulation of soluble guanylate cyclase reduces experimental dermal fibrosis. Ann Rheum Dis. 71(6): 1019-1026.

Beyer C, Zenzmaier C, Palumbo-Zerr K, Mancuso R, Distler A, Dees C, Zerr P, Huang J, Maier C, Pachowsky M L, Friebe A, Sandner P, Distler O, Schett G., Berger P, and Distler J H (2015). Stimulation of the soluble guanylate cyclase (sGC) inhibits fibrosis by blocking non-canonical TGFβ signalling. Ann Rheum Dis. 74(7):1408-1416.

Dees C, Beyer C, Distler A, Soare A, Zhang Y, Palumbo-Zerr K, Distler O, Schett G, Sandner P, and Distler J H (2015). Stimulators of soluble guanylate cyclase (sGC) inhibit experimental skin fibrosis of different aetiologies. Ann Rheum Dis. 74(8):1621-1625.

Evgenov O V, Pacher P, Schmidt P M, Haskó G, Schmidt H H, Stasch J P (2006). NO-independent stimulators and activators of soluble guanylate cyclase: discovery and therapeutic potential. Nat Rev Drug Discov. 2006; September; 5(9):755-768.

Follmann M, Ackerstaff J, Redlich G, Wunder F, Lang D, Kern A, Fey P, Griebenow N, Kroh W, Becker-Pelster E M, Kretschmer A, Geiss V, Li V, Straub A, Mittendorf J, Jautelat R, Schirok H, Schlemmer K H, Lustig K, Gerisch M, Knorr A, Tinel H, Mondritzki T, Trübel H, Sandner P, and Stasch J P (2017). Discovery of the Soluble Guanylate Cyclase Stimulator Vericiguat (BAY 1021189) for the Treatment of Chronic Heart Failure. J Med Chem. 60(12): 5146-5161.

Friebe A, Sandner P, Schmidtko A. Meeting report of the 8(th) International Conference on cGMP "cGMP: generators, effectors, and therapeutic implications" at Bamberg, Germany, from Jun. 23 to 25, 2017. Naunyn Schmiedebergs Arch Pharmacol; 390(12): 1177-1188.

Goh N S, Desai S R, Veeraraghavan S, Hansell D M, Copley S J, Maher T M, Corte T J, Sander C R, Ratoff J, Devaraj A, Bozovic G, Denton C P, Black C M, du Bois R M, and Wells A U (2008). Interstitial lung disease in systemic sclerosis: a simple staging system. Am J Respir Crit Care Med.; 177(11):1248-54.

Herrick A L et al. (2018) Patterns and predictors of skin score change in early diffuse systemic sclerosis from the European Scleroderma Observational Study. Ann Rheum Dis; doi: 10.1136/annrheumdis-2017-211912.

Khanna D, Furst E, Hays R D, Park G S, Wong W K, Seibold J R, Mayes M D, White B, Wigley F F, Weisman M, Barr W, Moreland L, Medsger Jr T A, Steen V D, Martin R W, Collier D, Weinstein A, Lally E V, Varga J, Weiner S R, Andrews B, Abeles M, Clements P J (2006). Minimally important difference in diffuse systemic sclerosis: Results from the D-penicillamine study, Annals of the Rheumatic Diseases 65(10):1325-9.

Khanna D and Denton C P (2010). Evidence-based management of rapidly progressing systemic sclerosis. Best. Pract. Res. Clin. Rheumatol. 24:387-400.

Khanna D, Nagaraja V, Tseng C H, Abtin F, Suh R, Kim G, et al. (2015) Predictors of lung function decline in scleroderma-related interstitial lung disease based on high-resolution computed tomography: implications for cohort enrichment in systemic sclerosis-associated interstitial lung disease trials. Arthritis Res Ther. 17:372.

Khanna D et al. (2017a) Safety and efficacy of subcutaneous tocilizumab in systemic sclerosis: results from the open-label period of a phase II randomised controlled trial (faSScinate). Ann Rheum Dis; 0:1-9. doi: 10.1136/annrheumdis-2017-211682.

Khanna D et al. (2017b) Standardization of the modified Rodnan skin score for use in clinical trials of systemic sclerosis. J Scleroderma Relat Disord. 2017; 2(1): 11-18. doi:10.5301/jsrd.5000231

Lopez S, Jahreis A, Sornasse T, Siegel J, Garg J, Khanna D, Lin C (2018). P322 Anti RNAPOL and TOPOI autoantibody reactivity and disease manifestations from the FaSScinate systemic sclerosis trial. Journal of Scleroderma and Related Disorders, Vol. 3(1S) 225-244 (p. 232).

Matei A E, Beyer C, Gyorfi A H, Soare A, Chen C W, Dees C, Bergmann C, Ramming A, Friebe A, Hofmann F, Distler O, Schett G, and Distler J H W (2018). Protein kinases G are essential downstream mediators of the antifibrotic effects of sGC stimulators. Ann Rheum Dis. 2017-212489. doi:10.1136 EPub ahead of print.

Maurer B, Graf N, Michel B A, et al. (2015). Prediction of worsening of skin fibrosis in patients with diffuse cutaneous systemic sclerosis using the EUSTAR database. Ann Rheum Dis; 74:1124-1131.

Ong V H and Denton C P (2010). Innovative therapies for systemic sclerosis. Curr. Opin. Rheumatol. 22:264-272.

Pigatto E, Ferranti M, Favaro M, Polito P, Zanatta E, Galozzi P, Tonello M, Punzi L, Cozzi F (2017). ANTI-RNA polymerase III subset of scleroderma patients: a monocentric study. 10.1136/annrheumdis-2017-eular.3292.

Schmidt H H, Schmidt P M, and Stasch J P (2009). NO- and haem-independent soluble guanylate cyclase activators. Handb Exp Pharmacol. (191):309-39.

Shah A A, Wigley F M (2013). My approach to the treatment of scleroderma. Mayo Clin Proc. 88(4):377-93.

Spiera R F et al. (2011). Imatinib mesylate (Gleevec) in the treatment of diffuse cutaneous systemic sclerosis: results of a 1-year, phase IIa, single-arm, open-label clinical trial. Ann. Rheum. Dis. 70:1003-1009. doi:10.1136/ard.2010.143974.

Stasch J P, Hobbs A J (2009). NO-independent, haem-dependent soluble guanylate cyclase stimulators. Handb Exp Pharmacol. 191:277-308.

Steen V D, Medsger T A, Jr (2000). Severe organ involvement in systemic sclerosis with diffuse scleroderma. Arthritis Rheum. 43(11):2437-44.

Terras S, Hartenstein H, Hoxtermann S, Gambichler T, Kreuter A (2016). RNA polymerase III autoantibodies may indicate renal and more severe skin involvement in systemic sclerosis. Int J Dermatol; 55:882-5.

Wu W, Jordan S, Graf N, Pena J, Curram J, Allanore Y, Matucci-Cerinic M, Pope J E, Denton C, Khanna D, Distler O (2017). Progression of Skin Fibrosis Is Associated with Decline of Lung Function in Patients with Diffuse Cutaneous Systemic Sclerosis: A European Scleroderma Trials and Research (EUSTAR) Analysis [abstract]. Arthritis Rheumatol. 2017; 69 (suppl 10). Paper is submitted to ARD.

Zenzmaier C, Kern J, Heitz M, Plas E, Zwerschke W, Mattesich M, Sandner P, and Berger P (2015). Activators and stimulators of soluble guanylate cyclase counteract myofibroblast differentiation of prostatic and dermal stromal cells. Exp Cell Res. 338(2):162-169.

The invention claimed is:

1. A method for preventing or delaying disease progression or for stabilizing disease in a subject suffering from diffuse cutaneous systemic sclerosis (dcSSc) comprising
   a. obtaining a measurement from the subject of at least one marker selected from the group consisting of the presence or absence of anti-RNA polymerase III autoantibodies, hsCRP at baseline, and FVC % predicted at baseline; and
   b. if the subject shows one or more of the presence of anti-RNA polymerase III autoantibodies, hsCRP at baseline of >3 mg/L, and FVC % predicted at baseline of 50-75, then administering a therapeutically effective amount of methyl 4,6-diamino-2-[1-(2-fluorobenzyl)-1H-pyrazolo[3,4-b]pyridin-3-yl]-5-pyrimidinyl(methyl)carbamate or a pharmaceutically acceptable salt thereof to the subject.

2. The method of claim 1, wherein the at least one marker measured is the presence or absence of anti-RNA polymerase III autoantibodies and if the subject shows the presence of anti-RNA polymerase III autoantibodies, then a therapeutically effective amount of methyl 4,6-diamino-2-[1-(2-fluorobenzyl)-1H-pyrazolo[3,4-b]pyridin-3-yl]-5-pyrimidinyl(methyl)carbamate or a pharmaceutically acceptable salt thereof is administered to the subject.

3. The method of claim 1, wherein the at least one marker measured is the FVC % predicted at baseline and if the subject shows FVC % predicted at baseline of 50-75, then a therapeutically effective amount of methyl 4,6-diamino-2-[1-(2-fluorobenzyl)-1H-pyrazolo[3,4-b]pyridin-3-yl]-5-pyrimidinyl(methyl)carbamate or a pharmaceutically acceptable salt thereof is administered to the subject.

4. The method of claim 1, wherein the at least one marker measured is hsCRP at baseline and if the subject shows hsCRP at baseline of >3 mg/L, then a therapeutically effective amount of methyl 4,6-diamino-2-[1-(2-fluorobenzyl)-1H-pyrazolo[3,4-b]pyridin-3-yl]-5-pyrimidinyl(methyl)carbamate or a pharmaceutically acceptable salt thereof is administered to the subject.

5. The method of claim 1, wherein the markers measured are the presence or absence of anti-RNA polymerase III autoantibodies, hsCRP at baseline, and FVC % predicted at baseline, and if the subject shows the presence of anti-RNA polymerase III autoantibodies, FVC % predicted at baseline of 50-75 and hsCRP at baseline of >3 mg/L, then a therapeutically effective amount of methyl 4,6-diamino-2-[1-(2-fluorobenzyl)-1H-pyrazolo[3,4-b]pyridin-3-yl]-5-pyrimidinyl(methyl)carbamate or a pharmaceutically acceptable salt thereof is administered to the subject.

6. The method of claim 1, wherein the prevention or delay of disease progression or stabilization of disease is shown by a higher degree of at least one of delaying or preventing progression or stabilizing of one or more of skin fibrosis, of dcSSc concomitant fibrosis of an internal organ selected from the group consisting of lung, kidney, heart, and blood vessels, and of decreasing the score of the HAQ-DI as compared to dcSSc subjects lacking one or more of the presence of anti-RNA polymerase III autoantibodies, hsCRP at baseline of >3 mg/L, and FVC % predicted at baseline of 50-75.

7. The method of claim 6, wherein the prevention or delay of disease progression or stabilization of disease is shown by a higher degree of delaying or preventing progression of or stabilizing skin fibrosis, measured as mRSS score.

8. The method of claim 6, wherein the prevention or delay of disease progression or stabilization of disease is shown by a higher degree of delaying or preventing progression of or stabilization of dcSSc concomitant fibrosis of the lung, measured as FVC % predicted.

9. The method of claim 6, wherein the prevention or delay of disease progression or stabilization of disease is shown by a higher degree of delaying or preventing progression or stabilization of dcSSc, measured by HAQ-DI.

10. The method of claim 6, wherein the prevention or delay of disease progression or stabilization of disease is shown by a higher degree of delaying or preventing progression of or stabilization of dcSSc measured as mRSS score and as FVC % predicted.

* * * * *